(12) United States Patent
Miller

(10) Patent No.: US 8,642,632 B2
(45) Date of Patent: *Feb. 4, 2014

(54) SELECTIVE ANDROGEN RECEPTOR MODULATORS

(75) Inventor: Chris P. Miller, Hingham, MA (US)

(73) Assignee: Radius Health, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/175,306

(22) Filed: Jul. 1, 2011

(65) Prior Publication Data

US 2012/0004270 A1    Jan. 5, 2012

Related U.S. Application Data

(60) Provisional application No. 61/361,168, filed on Jul. 2, 2010.

(51) Int. Cl.
*A61K 31/4245* (2006.01)
*C12N 5/071* (2010.01)
*G01N 33/53* (2006.01)
*C07D 271/10* (2006.01)

(52) U.S. Cl.
USPC ............ 514/364; 548/143; 435/375; 435/7.1

(58) Field of Classification Search
USPC .................... 514/364; 548/143; 435/375, 7.1
See application file for complete search history.

(56) References Cited

U.S. PATENT DOCUMENTS

| | | | |
|---|---|---|---|
| 5,411,981 A | 5/1995 | Gaillard-Kelly et al. | |
| 6,960,474 B2 | 11/2005 | Salvati et al. | |
| 8,067,448 B2* | 11/2011 | Miller | 514/364 |
| 8,268,872 B2* | 9/2012 | Miller | 514/364 |
| 8,455,525 B2 | 6/2013 | Miller | |
| 2005/0182105 A1 | 8/2005 | Nirschl et al. | |
| 2005/0250749 A1 | 11/2005 | Labrie et al. | |
| 2005/0261303 A1 | 11/2005 | Taniguchi et al. | |
| 2006/0106067 A1 | 5/2006 | Shiraishi et al. | |
| 2006/0142387 A1 | 6/2006 | Cadilla et al. | |
| 2006/0148893 A1 | 7/2006 | Blanc et al. | |
| 2006/0211756 A1 | 9/2006 | Zhang et al. | |
| 2006/0287327 A1 | 12/2006 | Labrie et al. | |
| 2007/0088039 A1 | 4/2007 | Balog et al. | |
| 2007/0281906 A1 | 12/2007 | Dalton et al. | |
| 2008/0057068 A1 | 3/2008 | Dalton et al. | |
| 2009/0042967 A1 | 2/2009 | Hasuoka | |
| 2009/0264534 A1 | 10/2009 | Dalton et al. | |
| 2010/0041721 A1 | 2/2010 | Miller | |
| 2011/0224267 A1* | 9/2011 | Miller | 514/363 |

FOREIGN PATENT DOCUMENTS

| | | |
|---|---|---|
| EP | 0 580 459 B1 | 3/2001 |
| JP | 60-16957 A | 1/1985 |
| JP | 01-261381 A | 10/1989 |
| WO | WO 96/41793 A1 | 12/1996 |
| WO | WO 97/49709 A1 | 12/1997 |
| WO | WO 02/16310 A1 | 2/2002 |
| WO | WO 03/011824 A1 | 2/2003 |
| WO | WO 03/068217 A1 | 8/2003 |
| WO | WO 03/096980 A2 | 11/2003 |
| WO | WO 2004/041277 A1 | 5/2004 |
| WO | WO 2004/041782 A1 | 5/2004 |
| WO | WO 2004/045518 A2 | 6/2004 |
| WO | WO 2004/080377 A2 | 9/2004 |
| WO | WO 2004/110978 A2 | 12/2004 |
| WO | WO 2005/000309 A2 | 1/2005 |
| WO | WO 2005/000794 A1 | 1/2005 |
| WO | WO 2005/000795 A2 | 1/2005 |
| WO | WO 2005/040136 A1 | 5/2005 |
| WO | WO 2005/042464 A1 | 5/2005 |
| WO | WO 2005/049574 A1 | 6/2005 |
| WO | WO 2005/049580 A1 | 6/2005 |
| WO | WO 2005/060956 A1 | 7/2005 |
| WO | WO 2005/077925 A1 | 8/2005 |
| WO | WO 2005/085185 A1 | 9/2005 |
| WO | WO 2005/086735 A2 | 9/2005 |
| WO | WO 2005/087232 A1 | 9/2005 |
| WO | WO 2005/089118 A2 | 9/2005 |
| WO | WO 2005/090282 A1 | 9/2005 |
| WO | WO 2005/090328 A1 | 9/2005 |
| WO | WO 2005/094810 A2 | 10/2005 |
| WO | WO 2005/099707 A1 | 10/2005 |
| WO | WO 2005/102998 A1 | 11/2005 |
| WO | WO 2005/108351 A1 | 11/2005 |
| WO | WO 2005/111028 A1 | 11/2005 |
| WO | WO 2005/115361 A2 | 12/2005 |
| WO | WO 2005/116001 A1 | 12/2005 |

(Continued)

OTHER PUBLICATIONS

Schafer et al. Drug Discovery Today, 2008, 13 (21/22), 913-916.*
Horig et al. Journal of Translational Medicine 2004, 2(44).*
Acevedo, S., et al., "Selective Androgen Receptor Modulators Antagonize Apolipoprotein E4-Induced Cognitive Impairments," *Letters in Drug Design & Discovery*, 5: 271-276 (2008).
Allan G. F., et al., "A Selective Androgen Receptor Modulator with Minimal Prostate Hypertrophic Activity Enhances Lean Body Mass in Male Rats and Stimulates Sexual Behavior in Female Rats," *Endocr.*, 32: 41-51 (2007).
Allan, G., et al., "A Selective Androgen Receptor Modulator that Reduces Prostate Tumor Size and Prevents Orchidectomy-Induced Bone Loss in Rats," *Journal of Steroid Biochemistry & Molecular Biology*, 103: 76-83 (2007).

(Continued)

*Primary Examiner* — Yong Chu
(74) *Attorney, Agent, or Firm* — Hamilton, Brook, Smith & Reynolds, P.C.

(57) ABSTRACT

This invention provides compounds as described herein or pharmaceutically acceptable salt thereof, pharmaceutical compositions comprising a compound as described herein or a pharmaceutically acceptable salt thereof and a pharmaceutically acceptable excipient, methods of modulating the androgen receptor using the compounds or compositions described herein, methods of treating diseases beneficially treated by an androgen receptor modulator (e.g., sarcopenia, prostate cancer, contraception, type 2 diabetes related disorders or diseases, anemia, depression, and renal disease) using the compounds and compositions described herein and processes for making compounds described herein and intermediates useful in the preparation of same.

26 Claims, 1 Drawing Sheet

(56) References Cited

FOREIGN PATENT DOCUMENTS

| WO | WO 2005/120483 A2 | 12/2005 |
|---|---|---|
| WO | WO 2006/039243 A1 | 4/2006 |
| WO | WO 2006/044359 A2 | 4/2006 |
| WO | WO 2006/044707 A1 | 4/2006 |
| WO | WO 2006/055184 A2 | 5/2006 |
| WO | WO 2006/060108 A1 | 6/2006 |
| WO | WO 2006/076317 A2 | 7/2006 |
| WO | WO 2006/113552 A2 | 10/2006 |
| WO | WO 2006/124447 A2 | 11/2006 |
| WO | WO 2006/133216 A2 | 12/2006 |
| WO | WO 2007/002181 A2 | 1/2007 |
| WO | WO 2007/005887 A2 | 1/2007 |
| WO | WO 2007/015567 A1 | 2/2007 |
| WO | WO 2007/034846 A1 | 3/2007 |
| WO | WO 2007/067490 A1 | 6/2007 |
| WO | WO 2007/087518 A2 | 8/2007 |
| WO | WO 2007/099200 A1 | 9/2007 |
| WO | WO 2007/146914 A1 | 12/2007 |
| WO | WO 2008/008433 A2 | 1/2008 |
| WO | WO 2008/011072 A2 | 1/2008 |
| WO | WO 2008/011073 A1 | 1/2008 |
| WO | WO 2008/024456 A2 | 2/2008 |
| WO | WO 2008/042571 A2 | 4/2008 |
| WO | WO 2008/044033 A1 | 4/2008 |
| WO | WO 2008/063867 A2 | 5/2008 |
| WO | WO 2008/121602 A1 | 10/2008 |
| WO | WO 2008/124000 A2 | 10/2008 |
| WO | WO 2008/124922 A1 | 10/2008 |
| WO | WO 2008/127717 A1 | 10/2008 |
| WO | WO 2008/128100 A1 | 10/2008 |
| WO | WO 2009/081197 A1 | 7/2009 |
| WO | WO 2009/082437 A2 | 7/2009 |
| WO | WO 2009/105214 A2 | 8/2009 |
| WO | WO 2009/133861 A1 | 11/2009 |
| WO | WO 2009/140448 A1 | 11/2009 |

OTHER PUBLICATIONS

Autoimmune disorders: MedlinePlus Medical Encyclopedia [online], [retrieved on Jun. 3, 2011]. Retrieved from the Internet URL: http://www.nlm.nih.gov/medlineplus/ency/article/000816.htm.

Bohl, C.E., et al., "Structural Basis for Accommodation of Nonsteroidal Ligands in the Androgen Receptors," *The Journal of Biological Chemistry*, 280 (45): 37747-37754 (Nov. 11, 2005).

Bohl, C. E., "Structural Basis for Antagonism and Resistance of Bicalutamide in Prostate Cancer," *PNAS*, 102 (17): 6201-6206 (2005).

Cantin, L., et al., "Structural Characterization of the Human Androgen Receptor Ligand-Binding Domain Complexed with EM5744, a Rationally Designed Steroidal Ligand Bearing a Bulky Chain Directed Toward Helix 12," *Journal of Biological Chemistry*, 282 (42): 30910-30919 (Oct. 19, 2007).

Gao, W., et al., "Ockham's Razor and Selective Androgen Receptor Modulators (SARMs): Are we Overlooking the Role of 5α-Reductase?", *Molecular Interventions*, 7: 10-13 (Feb. 2007).

Gao, W., et al., "Expanding the Therapeutic use of Androgens via Selective Androgen Receptor Modulators (SARMs)," *Drug Discovery Today*, 12: 241-248 (Mar. 2007).

Gao, W., et al., "Selective Androgen Receptor Modulator (SARM) Treatment Improves Muscle Strength," *Endocrinology*, doi:10.1210/en.2005-0572, pp. 1-37 (Aug. 11, 2005).

Gao, W., et al., "Comparison of the Pharmacological Effects of a Novel Selective Androgen Receptor Modulator, the 5α-Reductase Inhibitor Finasteride, and the Antiandrogen Hydroxyflutamide in Intact Rats: New Approach for Benign Prostate Hyperplasia,"*Endocrinology*, 145 (12): 5420-5428 (Dec. 2004).

Gao, W., et al., "Selective Androgen Receptor Modulator Treatment Improves Muscle Strength and Body Composition and Prevents Bone Loss in Orchidectomized Rats," *Endocrinology*, 146 (11): 4887-4897 (Nov. 2005).

Hamann, L. G., "Discovery and Preclinical Profile of a Highly Potent and Muscle Selective Androgen Receptor Modulator (SARM)," 227th National Meeting of the American Chemical Society Medicinal Chemistry Division, Mar. 28, 2004, Anaheim, CA.

Hamann, L.G., et al., "Tandem Optimization of Target Activity and Elimination of Mutagenic Potential in a Potent Series of N-aryl Bicyclic Hydantoin-Based Selective Androgen Receptor Modulators," *Bioorganic & Medicinal Chemistry Letters*, 17: 1860-1864 (2007).

Hanada, K., et al. "Bone Anabolic Effects of S-40503, a Novel Nonsteroidal Selective Androgen Receptor Modulator (SARM), in Rat Models of Osteoporosis," *Biol. Pharm. Bull.*, 26(11): 1563-1569 (Nov. 2003).

Higuchi, R. I., et al., "Novel Series of Potent, Nonsteroidal, Selective Androgen Receptor Modulators Based on 7 H-[1,4]Oxazino[3,2-g]quinolin-7-ones," *J. Med. Chem.*, 50(10): 2486-2496 (2007).

Higuchi, R. I., et al.,"Novel Series of Potent, Nonsteroidal, Selectve Androgen Receptor Modulators Based on 7H-[1,4]Oxazino[3,2-g]quinolin-7-ones," *Journal of Medicinal Chemistry*, pp. A-K (Apr. 17, 2007).

Hwang, D. J., et al., "Arylisothiocyanato Selective Androgen Receptor Modulators (SARMs) for Prostate Cancer," *Bioorganic & Medicinal Chemistry*, 14: 6525-6538 (2006).

Kemppainen, J. A., et al., "Distinguishing Androgen Receptor Agonists and Antagonists: Distinct Mechanisms of Activation by Medroxyprogesterone Acetate and Dihydrotestosterone," *Molecular Endocrinology*, 13: 440-454 (1999).

Kilbourne, E. J., et al., "Selective Androgen Receptor Modulators for Frailty and Osteoporosis," *Current Opinion in Investigational Drugs*, 8(10): 821-829 (2007).

Kim, J., et al., "The 4-Para Substituent of S-3-(phenoxy)-2-hydroxy-2-methyl-N-(4-nitro-3-trifluoromethyl-phenyl)-propionamides is a Major Structural Determinant of In Vivo Disposition and Activity of Selective Androgen Receptor Modulators," *JPET* #88344, DOI:10.1124/jpet.105.088344, 42 pages (Jun. 29, 2005).

Kinoyama, I., et al.,"(+)-(2R,5S)-4-[4-Cyano-3-(trifluorornethyl)phenyl]-2,5-dimethyl-N-[6-(trifluoromethyl)pyridin-3-yl]piperazine-1-carboxamide (YM580) as an Orally Potent and Peripherally Selective Nonsteroidal Androgen Receptor Antagonist," *J. Med. Chem.* 49(2): 716-726 (2006).

Lanter, J. C., et al., "The Discovery of a Potent Orally Efficacious Indole Androgen Receptor Antagonist Through in vivo Screening," *Bioorganic & Medicinal Chemistry Letters*, 17: 123-126 (2007).

Martinborough, E., et al.,"Substituted 6-(1-(Pyrrolidine)quinolin-2(1H)-ones as Novel Selective Androgen Receptor Modulators," *J. Med. Chem.* 50(21): 5049-5052 (Oct. 18, 2007).

McGinley, P. L., et al., "Circumventing Anti-Androgen Resistance by Molecular Design," *J. Am. Chem. Soc.*, 129: 3822-3823 (2007).

Miller, C.P., et al., "Synthesis of Potent, Substituted Carbazoles as Selective Androgen Receptor Modulators (SARMs)," *Bioorg. Med. Chem. Lett.* 20: 7516-7520 (2010).

Miller, C. P., et al., "Design, Synthesis, and Preclinical Characterization of the Selective Androgen Receptor Modulator (SARM) RAD140,"*ACS Med. Chem. Lett.*, XXXX, XXX, DOI: 10.1021/ml1002508, pp. A-F (Dec. 2, 2010).

Mitchell, H. J., et al., Design, Synthesis, and Biological Evaluation of 16-Substituted 4-Azasteroids as Tissue-Selective Androgen Receptor Modulators (SARMs), *J. Med. Chem.*, XXXX, vol. XXX, No. XX, pp. A-D (2009).

Mohler, M. L., et al., "Nonsteroidal Selective Androgen Receptor Modulators (SARMs):Dissociating the Anabolic and Androgenic Activities of the Androgen Receptor for Therapeutic Benefit," *J. Med Chem.*, XXXX, vol. XXX, No. XX, pp. A-T (May 11, 2009).

Morris, J. J., et al., "Non-steroidal Antiandrogens. Design of Novel Compounds Based on an Infrared Study of the Dominant Conformation and Hydrogen-Bonding Properties of a Series of Anilide Antiandrogens," *J. Med. Chem.*, 34: 447-455 (1991).

Ng, R. A., "Synthesis and SAR of Potent and Selective Androgen Receptor Antagonists: 5,6-Dicholoro-benzimidazole Derivatives," *Bioorganic & Medicinal Chemistry Letters*, 17: 784-788 (2007).

(56) References Cited

OTHER PUBLICATIONS

Ng, R. A., "Synthesis of Potent and Tissue-Selective Androgen Receptor Modulators (SARMs): 2-(2,2,2)-Trifluoroethyl-benzimidazole Scaffold," *Bioorganic & Medicinal Chemistry Letters*, 17: 1784-1787 (2007).

Ostrowski, J., et al., "Pharmacological and X-Ray Structural Characterization of a Novel Selective Androgen Receptor Modulator: Potent Hyperanabolic Stimulation of Skeletal Muscle with Hypostimulation of Prostate in Rats," *Endocrinology*, 148(1): 4-12 (Jan. 2007).

Piu, F., et al., "Pharmacological Characterization of AC-262536, A Novel Selective Androgen Receptor Modulator," *Journal of Steroid Biochemistry & Molecular Biology*, 109: 129-137 (2008).

Salvati, M. E., et al., "Identification and Optimization of a Novel Series of [2.2.1]-oxabicyclo imide-based Androgen Receptor Antagonists," *Bioorganic & Medicinal Chemistry Letters*, 18: 1910-1915 (2008).

Sun, C., et al. "Discovery of Potent, Orally-Active, and Muscle-Selective Androgen Receptor Modulators Based on an *N*-Aryl-hydroxybicyclohydantoin Scaffold," *J. Med. Chem.* 49(26): 7596-7599 (2006).

Tucker, H., et al., "Nonsterodial Antiandrogens, Synthesis and Structure-Activity Relationships of 3-Substituted Derivatives of 2-Hydroxypropionanilides," *J. Med. Chem.*, 31: 954-959 (1988).

Vajda, E. G., et al., Pharmacokinetics and Pharmacodynamics of LGD-3303 [9-Cholor-2-ethyl-1-methyl-3-(2,2,2-trifluoroethyl)-3*H*-pyrrolo-[3,2-*f*]quinolin-7(6*H*)-one], an Orally Available Nonsteroidal-Selective Androgen Receptor Modulator, *The Journal of Pharmacology and Experimental Therapeutics*, 328(2): 663-670 (2009).

Van Oeveren, A., et al., "Novel Selective Androgen Receptor Modulators: SAR Studies on 6-bisalkylamino-2-quinolinones," *Bioorganic & Medicinal Chemistry Letters*, 17: 1527-1531 (2007).

Wang, Z. et al., "Anti-Inflammatory Properties and Regulatory Mechanism of a Novel Derivative of Artemisinin in Experimental Autoimmune Encephalomyelitis," *The Journal of Immunology, J Immunol* 179;5958-5965 (2007).

Zeng, C., et al., "Efficient Synthesis of (2R,3S)-2-amino-3-(benzyloxy)-4,4,4-trifluorobutanoic acid (4,4,4-trifluoro-OBn-D-*al*-*l*othreonine)," *Tetrahedron Letters*, 51: 5361-5363 (2010).

Zhang, X., et al., "Design, Synthesis, and in Vivo SAR of a Novel Series of Pyrazolines as Potent Selective Androgen Receptor Modulators," *J. Med. Chem*, 50(16): 3857-3869 (2007).

Zhang, X., et al., "Synthesis and SAR of Novel Hydantoin Derivatives as Selective Androgen Receptor Modulators," *Bioorganic & Medicinal Chemistry Letters*, 16: 5763-5766 (2006).

Notification of Transmittal of International Search Report and The Written Opinion of the International Searching Authority, or The Declaration, dated Aug. 7, 2009, International Application No. PCT/US2009/001035.

Notification Concerning Transmittal of International Preliminary Report on Patentability, dated Sep. 2, 2010, International Application No. PCT/US2009/001035.

Non-Final Office Action for U.S. Appl. No. 12/541,489, Mailing Date: Oct. 25, 2011.

Notice of Allowance for U.S. Appl. No. 12/378,812, Mailing Date: Jul. 21, 2011.

Notice of Allowance in related U.S. Appl. No. 12/541,489, date mailed: May 10, 2012.

English language abstract in publication No. GB1547758 A, which corresponds to Japanese patent laid-open No. JP 60-16957 A.

Office Action dated Sep. 12, 2012 in U.S. Application No. 2011/0224267.

Notice of Allowance dated Feb. 1, 2013 in U.S. Application No. 2011/0224267.

Notice of Allowance, U.S. Appl. No. 13/570,417, Dated: Sep. 17, 2013.

* cited by examiner

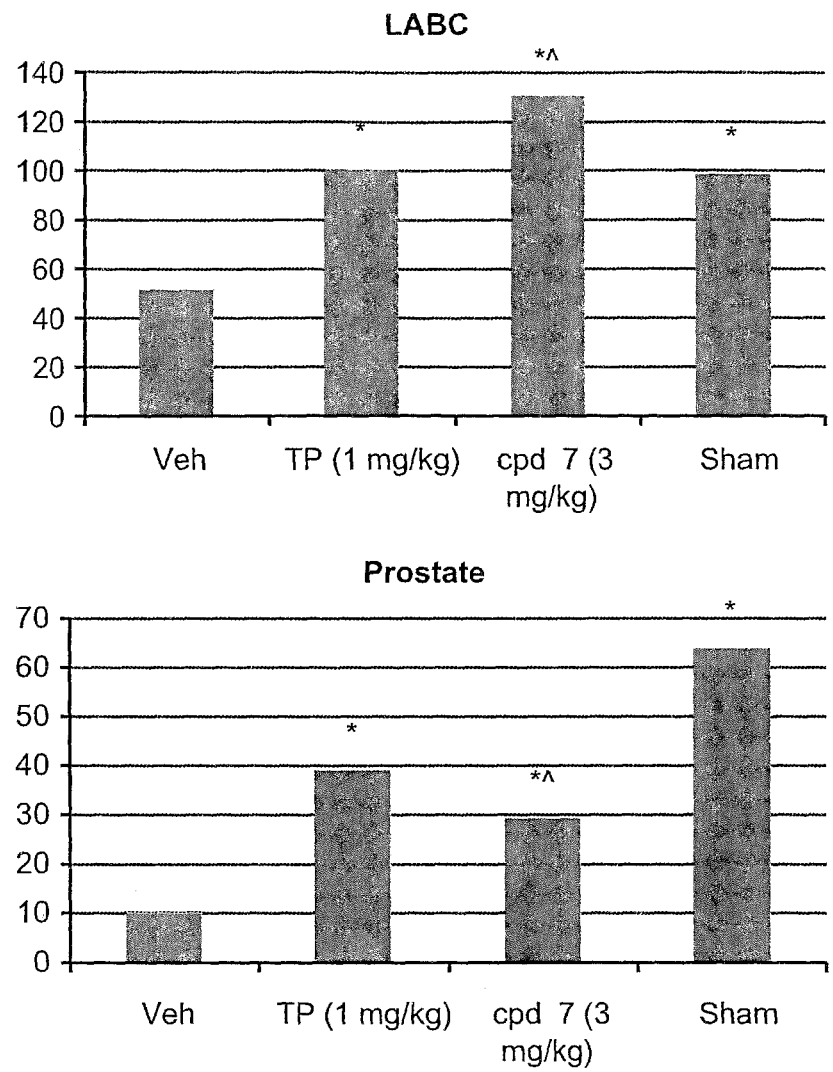

SELECTIVE ANDROGEN RECEPTOR MODULATORS

This application claims the benefit of U.S. Provisional Application No. 61/361,168, filed on Jul. 2, 2010. The entire teachings of the above application are incorporated herein by reference.

BACKGROUND OF THE INVENTION

Androgen signaling is mediated through the androgen receptor (AR) and is a nuclear signaling pathway of tremendous importance in mammals. In addition to its primary role in sexual development, maturation and maintenance of sexual function in both males and females, this critical hormone signaling pathway affects a large number of non-sexual tissues including, bone, muscle, CNS, liver, etc. In humans, testosterone and dihydrotestosterone are the primary ligands that mediate AR-signaling. Both are high affinity ligands for AR, with dihydrotestosterone having somewhat higher affinity. Testosterone is converted to dihydrotestosterone through the action of 5α-reductase enzymes and is converted to 17β-estradiol (potent endogenous estrogen) through the action of P-450 aromatase enzymes. AR signaling is mediated by binding of an AR ligand to AR in the cellular cytosol, homodimerization of two AR receptors and nuclear location of the ligand bound dimer to the cell nucleus where the complex associates with various coactivators as well as Androgen Response Elements (palindrome-like sequences of DNA) which serve as activation sites for certain AR-mediated genes. Due to the very large number of AR target tissues, both sexual and non-sexual, androgens such as testosterone and dihydrotestosterone have a number of potentially desirable actions as well as non-desirable actions depending on the particular individual's age, sex, therapeutic need, etc. In the adult male and female, certain positive consequences of AR-agonist signaling can be generalized as including increased bone mineral density and a corresponding reduction of risk of bone fractures. Accordingly, androgen supplementation can be very valuable in the prevention or treatment of osteoporosis where the osteoporosis might originate from any number of different causes, such as corticosteroid induced osteoporosis and age-related osteoporosis (e.g. post-menopausal). Likewise, males and females respond to agonist supplementation with an increase in muscle mass and very often a decrease in fat mass. This is beneficial in a very large number of treatment modalities. For example, there are many wasting syndromes associated with different disease states where the therapeutic goal is for a patient to maintain weight and function, such as the treatment of cancer associated cachexia, AIDs-related cachexia, anorexia and many more. Other muscle-wasting disorders such as muscular dystrophy in its many forms as well as related disorders can also be treated to advantage with androgens. The increase in muscle mass with concomitant reduction in fat mass associated with anabolic androgen action has additional health benefits for many men and women including potentially increased sensitivity to insulin. Androgen supplementation is also associated with reduction of high triglycerides, though there is a general correlation with androgen use and decreased HDL levels and in some cases, increased LDL levels. In the CNS, numerous laudatory benefits have been associated with androgen supplementation including improved sexual desire and functioning, increased cognition, memory, sense of well being and possible decrease in risk of Alzheimer's disease.

Androgen antagonists have been used in treating prostate cancer, where blockade of androgen signaling is desired whereas some androgens agonists (e.g. dihydrotestosterone) stimulate the hypertrophy of prostate tissue and may be a causative factor in prostate cancer. Androgen agonist activity is often associated with stimulation of benign prostate hyperplasia, a disease characterized by an enlarged prostate often accompanied by discomfort and difficulty in urination due to blockage of the urethra. As a result, androgen antagonists have efficacy in the reduction of the size of the prostate and the corresponding symptoms of benign prostate hyperplasia, though it is much more common to use a 5α-reductase inhibitor (e.g. finasteride) as such inhibitors do not decrease androgen signaling systemically to the same extent as a typical anti-androgen (e.g. bicalutamide), but rather reduce androgen drive more site specifically to where testosterone to DHT conversion occurs such as the prostate and scalp. Androgen antagonists also find utility in the treatment of hirsutism in women as well as the treatment of acne. Androgens are generally contraindicated in conditions that are treated with androgen antagonists since they can exacerbate the symptoms that are being treated.

Ideally, an androgen would retain the benefits of androgen agonists while minimizing the stimulatory effects on the prostate in males as well as some of the other untoward effects of androgens including masculinization of women and increase in acne in both sexes. Androgens that demonstrate tissue selective effects compared to the benchmarks testosterone and/or dihydrotestosterone are typically referred to as androgen receptor modulators or more often, selective androgen receptor modulators (SARMs). At the far end of potential selectivity, an ideal SARM would demonstrate no prostate stimulation while maintaining or growing muscle sufficient to effectively mimic the effects of testosterone or dihydrotestosterone. The growing appreciation of the positive contribution that SARMs can make in the many therapeutic areas where androgen activity is desirable has led to a large amount of research into this important area. Due to a compelling need for novel and effective androgen therapies with potentially reduced side effects, novel and effective SARM compounds are urgently needed.

SUMMARY OF THE INVENTION

In certain embodiments, this invention describes a compound selected from:
(R)-4-(1-(5-(4-fluorophenyl)-1,3,4-oxadiazol-2-yl)-2-hydroxy-2-methylpropylamino)-2-(trifluoromethyl)benzonitrile;
(R)-4-(1-(5-(4-fluorophenyl)-1,3,4-oxadiazol-2-yl)-2-hydroxy-2-methylpropylamino)-3-methyl-2-(trifluoromethyl)benzonitrile;
(R)-4-(1-(5-(4-cyanophenyl)-1,3,4-oxadiazol-2-yl)-2-hydroxy-2-methylpropylamino)-3-methyl-2-(trifluoromethyl)benzonitrile;
2-Chloro-4-((1R,2S)-1-(5-(4-cyanophenyl)-1,3,4-oxadiazol-2-yl)-2-hydroxypropylamino)-3-propylbenzonitrile;
(R)-2-chloro-4-(1-(5-(4-fluorophenyl)-1,3,4-oxadiazol-2-yl)-2-hydroxy-2-methylpropylamino)-3-methylbenzonitrile;
(R)-2-chloro-4-(1-(5-(4-cyanophenyl)-1,3,4-oxadiazol-2-yl)-2-hydroxy-2-methylpropylamino)-3-methylbenzonitrile; and
2-chloro-4-((1R,2S)-1-(5-(4-cyanophenyl)-1,3,4-oxadiazol-2-yl)-3,3,3-trifluoro-2-hydroxypropylamino)-3-methylbenzonitrile
or pharmaceutically acceptable salt of any of the foregoing.

BRIEF DESCRIPTION OF THE DRAWING

The FIGURE shows the effect of the compound of Example 7 (Cpd 7) on levator ani muscle (LABC) and prostate weight in treated, castrated rats. Organ and muscle weight is on Y-axis and the numbers refer to weight in milligrams. *$p<0.05$ compared to vehicle. ^$p<0.05$ compared to TP and sham.

DETAILED DESCRIPTION OF THE INVENTION

In certain embodiments, this invention describes a compound selected from:

(R)-4-(1-(5-(4-fluorophenyl)-1,3,4-oxadiazol-2-yl)-2-hydroxy-2-methylpropylamino)-2-(trifluoromethyl)benzonitrile;

(R)-4-(1-(5-(4-fluorophenyl)-1,3,4-oxadiazol-2-yl)-2-hydroxy-2-methylpropylamino)-3-methyl-2-(trifluoromethyl)benzonitrile;

(R)-4-(1-(5-(4-cyanophenyl)-1,3,4-oxadiazol-2-yl)-2-hydroxy-2-methylpropylamino)-3-methyl-2-(trifluoromethyl)benzonitrile;

2-Chloro-4-((1R,2S)-1-(5-(4-cyanophenyl)-1,3,4-oxadiazol-2-yl)-2-hydroxypropylamino)-3-propylbenzonitrile;

(R)-2-chloro-4-(1-(5-(4-fluorophenyl)-1,3,4-oxadiazol-2-yl)-2-hydroxy-2-methylpropylamino)-3-methylbenzonitrile;

(R)-2-chloro-4-(1-(5-(4-cyanophenyl)-1,3,4-oxadiazol-2-yl)-2-hydroxy-2-methylpropylamino)-3-methylbenzonitrile; and 2-chloro-4-((1R,2S)-1-(5-(4-cyanophenyl)-1,3,4-oxadiazol-2-yl)-3,3,3-trifluoro-2-hydroxypropylamino)-3-methylbenzonitrile, or pharmaceutically acceptable salt of any of the foregoing.

In certain embodiments, this invention describes a compound selected from:

2-Chloro-4-((1R,2S)-1-(5-(4-cyanophenyl)-1,3,4-oxadiazol-2-yl)-2-hydroxypropylamino)-3-propylbenzonitrile;

(R)-2-chloro-4-(1-(5-(4-fluorophenyl)-1,3,4-oxadiazol-2-yl)-2-hydroxy-2-methylpropylamino)-3-methylbenzonitrile; and (R)-2-chloro-4-(1-(5-(4-cyanophenyl)-1,3,4-oxadiazol-2-yl)-2-hydroxy-2-methylpropylamino)-3-methylbenzonitrile, or a pharmaceutically acceptable salt of any of the foregoing.

In a particular embodiment, the compound is 2-chloro-4-((1R,2S)-1-(5-(4-cyanophenyl)-1,3,4-oxadiazol-2-yl)-3,3,3-trifluoro-2-hydroxypropylamino)-3-methylbenzonitrile or pharmaceutically acceptable salt thereof.

The compound names in the list were generated with the assistance of ChemDraw® versions 8.0, 9.0 and/or 11.0 (CambridgeSoft Corporation, 100 CambridgePark Drive, Cambridge, Mass. 02140 USA). When the stereochemistry at a chiral center is not defined in the compound name this indicates that the sample prepared contained a mixture of isomers at this center.

The invention also relates to pharmaceutical compositions comprising a compound selected from:

(R)-4-(1-(5-(4-fluorophenyl)-1,3,4-oxadiazol-2-yl)-2-hydroxy-2-methylpropylamino)-2-(trifluoromethyl)benzonitrile;

(R)-4-(1-(5-(4-fluorophenyl)-1,3,4-oxadiazol-2-yl)-2-hydroxy-2-methylpropylamino)-3-methyl-2-(trifluoromethyl)benzonitrile;

(R)-4-(1-(5-(4-cyanophenyl)-1,3,4-oxadiazol-2-yl)-2-hydroxy-2-methylpropylamino)-3-methyl-2-(trifluoromethyl)benzonitrile;

2-Chloro-4-((1R,2S)-1-(5-(4-cyanophenyl)-1,3,4-oxadiazol-2-yl)-2-hydroxypropylamino)-3-propylbenzonitrile;

(R)-2-chloro-4-(1-(5-(4-fluorophenyl)-1,3,4-oxadiazol-2-yl)-2-hydroxy-2-methylpropylamino)-3-methylbenzonitrile;

(R)-2-chloro-4-(1-(5-(4-cyanophenyl)-1,3,4-oxadiazol-2-yl)-2-hydroxy-2-methylpropylamino)-3-methylbenzonitrile; and 2-chloro-4-((1R,2S)-1-(5-(4-cyanophenyl)-1,3,4-oxadiazol-2-yl)-3,3,3-trifluoro-2-hydroxypropylamino)-3-methylbenzonitrile, or pharmaceutically acceptable salt of any of the foregoing and at least one pharmaceutically acceptable excipient.

The invention also provides a method of modulating an androgen receptor in a cell, comprising the administration of a compound to said cell wherein said compound is selected from:

(R)-4-(1-(5-(4-fluorophenyl)-1,3,4-oxadiazol-2-yl)-2-hydroxy-2-methylpropylamino)-2-(trifluoromethyl)benzonitrile;

(R)-4-(1-(5-(4-fluorophenyl)-1,3,4-oxadiazol-2-yl)-2-hydroxy-2-methylpropylamino)-3-methyl-2-(trifluoromethyl)benzonitrile;

(R)-4-(1-(5-(4-cyanophenyl)-1,3,4-oxadiazol-2-yl)-2-hydroxy-2-methylpropylamino)-3-methyl-2-(trifluoromethyl)benzonitrile;

2-Chloro-4-((1R,2S)-1-(5-(4-cyanophenyl)-1,3,4-oxadiazol-2-yl)-2-hydroxypropylamino)-3-propylbenzonitrile;

(R)-2-chloro-4-(1-(5-(4-fluorophenyl)-1,3,4-oxadiazol-2-yl)-2-hydroxy-2-methylpropylamino)-3-methylbenzonitrile;

(R)-2-chloro-4-(1-(5-(4-cyanophenyl)-1,3,4-oxadiazol-2-yl)-2-hydroxy-2-methylpropylamino)-3-methylbenzonitrile; and 2-chloro-4-((1R,2S)-1-(5-(4-cyanophenyl)-1,3,4-oxadiazol-2-yl)-3,3,3-trifluoro-2-hydroxypropylamino)-3-methylbenzonitrile, or pharmaceutically acceptable salt of any of the foregoing.

This invention provides a method of identifying a compound capable of modulating an androgen receptor comprising contacting a cell expressing an androgen receptor with a compound selected from:

(R)-4-(1-(5-(4-fluorophenyl)-1,3,4-oxadiazol-2-yl)-2-hydroxy-2-methylpropylamino)-2-(trifluoromethyl)benzonitrile;

(R)-4-(1-(5-(4-fluorophenyl)-1,3,4-oxadiazol-2-yl)-2-hydroxy-2-methylpropylamino)-3-methyl-2-(trifluoromethyl)benzonitrile;

(R)-4-(1-(5-(4-cyanophenyl)-1,3,4-oxadiazol-2-yl)-2-hydroxy-2-methylpropylamino)-3-methyl-2-(trifluoromethyl)benzonitrile;

2-Chloro-4-((1R,2S)-1-(5-(4-cyanophenyl)-1,3,4-oxadiazol-2-yl)-2-hydroxypropylamino)-3-propylbenzonitrile;

(R)-2-chloro-4-(1-(5-(4-fluorophenyl)-1,3,4-oxadiazol-2-yl)-2-hydroxy-2-methylpropylamino)-3-methylbenzonitrile;

(R)-2-chloro-4-(1-(5-(4-cyanophenyl)-1,3,4-oxadiazol-2-yl)-2-hydroxy-2-methylpropylamino)-3-methylbenzonitrile; and 2-chloro-4-((1R,2S)-1-(5-(4-cyanophenyl)-1,3,4-oxadiazol-2-yl)-3,3,3-trifluoro-2-hydroxypropylamino)-3-methylbenzonitrile, or pharmaceutically acceptable salt of any of the foregoing and monitoring the effect of the compound on the cell.

This invention also provides a method of treating (e.g., preventing, or ameliorating the symptoms associated with, or reducing the incidence of, reducing the pathogenesis of, facilitating the recovery from or delaying the onset of) a disease, syndrome, illness, or symptom associated with insufficient androgen levels in a mammal in need thereof, wherein said method comprises the administration to said mammal of an effective amount of a compound selected from:

(R)-4-(1-(5-(4-fluorophenyl)-1,3,4-oxadiazol-2-yl)-2-hydroxy-2-methylpropylamino)-2-(trifluoromethyl)benzonitrile;

(R)-4-(1-(5-(4-fluorophenyl)-1,3,4-oxadiazol-2-yl)-2-hydroxy-2-methylpropylamino)-3-methyl-2-(trifluoromethyl)benzonitrile;

(R)-4-(1-(5-(4-cyanophenyl)-1,3,4-oxadiazol-2-yl)-2-hydroxy-2-methylpropylamino)-3-methyl-2-(trifluoromethyl)benzonitrile;

2-Chloro-4-((1R,2S)-1-(5-(4-cyanophenyl)-1,3,4-oxadiazol-2-yl)-2-hydroxypropylamino)-3-propylbenzonitrile;

(R)-2-chloro-4-(1-(5-(4-fluorophenyl)-1,3,4-oxadiazol-2-yl)-2-hydroxy-2-methylpropylamino)-3-methylbenzonitrile;

(R)-2-chloro-4-(1-(5-(4-cyanophenyl)-1,3,4-oxadiazol-2-yl)-2-hydroxy-2-methylpropylamino)-3-methylbenzonitrile; and 2-chloro-4-((1R,2S)-1-(5-(4-cyanophenyl)-1,3,4-oxadiazol-2-yl)-3,3,3-trifluoro-2-hydroxypropylamino)-3-methylbenzonitrile, or pharmaceutically acceptable salt of any of the foregoing, or a pharmaceutical composition as described herein. In a particular embodiment, the mammal is a human.

In some embodiments, this invention provides a method of treating (e.g., preventing, or ameliorating the symptoms associated with, or reducing the incidence of, reducing the pathogenesis of, facilitating the recovery from or delaying the onset of) sarcopenia, frailty, multiple sclerosis, osteoporosis, anemia, cognitive impairment, cachexia, muscular dystrophy, weak appetite, low body weight, anorexia nervosa, acne, seborrhea, polycystic ovarian syndrome, hair loss, AIDs wasting, chronic fatigue syndrome, short stature, low testosterone levels, diminished libido, benign prostate hypertrophy, infertility, erectile dysfunction, vaginal dryness, premenstrual syndrome, postmenopausal symptoms, female hormone replacement therapy, male hormone replacement therapy, depression, Type II diabetes, mood disorders, sleep disorders, memory disorders, neurodegenerative disorders, Alzheimer's dementia, attention deficit disorder, senile dementia, coronary artery disease, hirsutism, pain, myalgia, myocardial infarction, stroke, clotting disorders, thromboembolisms, congestive heart disorder, low insulin sensitivity, low glucose utilization, high blood sugar, organ transplant, metabolic syndrome, diabetes, glucose intolerance, hyperinsulinemia, insulin resistance, tooth injury, tooth disease, periodontal disease, liver disease, thrombocytopenia, fatty liver conditions, endometriosis, hot flushes, hot flashes, vasomotor disturbance, stress disorders, dwarfism, dyslipidemia, cardiovascular disease, coronary artery disease, renal disease, thin skin disorders, lethargy, osteopenia, dialysis, irritable bowel syndrome, Crohn's disease, Paget's disease, osteoarthritis, connective tissue disease or disorders, injury, burns, trauma, wounds, bone fracture, atherosclerosis, cachexia, cancer cachexia, and obesity, in a mammal in need thereof comprising the administration to said mammal of an effective amount of a compound selected from:

(R)-4-(1-(5-(4-fluorophenyl)-1,3,4-oxadiazol-2-yl)-2-hydroxy-2-methylpropylamino)-2-(trifluoromethyl)benzonitrile;

(R)-4-(1-(5-(4-fluorophenyl)-1,3,4-oxadiazol-2-yl)-2-hydroxy-2-methylpropylamino)-3-methyl-2-(trifluoromethyl)benzonitrile;

(R)-4-(1-(5-(4-cyanophenyl)-1,3,4-oxadiazol-2-yl)-2-hydroxy-2-methylpropylamino)-3-methyl-2-(trifluoromethyl)benzonitrile;

2-Chloro-4-((1R,2S)-1-(5-(4-cyanophenyl)-1,3,4-oxadiazol-2-yl)-2-hydroxypropylamino)-3-propylbenzonitrile;

(R)-2-chloro-4-(1-(5-(4-fluorophenyl)-1,3,4-oxadiazol-2-yl)-2-hydroxy-2-methylpropylamino)-3-methylbenzonitrile;

(R)-2-chloro-4-(1-(5-(4-cyanophenyl)-1,3,4-oxadiazol-2-yl)-2-hydroxy-2-methylpropylamino)-3-methylbenzonitrile; and 2-chloro-4-((1R,2S)-1-(5-(4-cyanophenyl)-1,3,4-oxadiazol-2-yl)-3,3,3-trifluoro-2-hydroxypropylamino)-3-methylbenzonitrile, or pharmaceutically acceptable salt of any of the foregoing or a pharmaceutical composition as described herein. In a particular embodiment, the mammal is a human.

In certain aspects, this invention describes a method of treating (e.g., preventing, or ameliorating the symptoms associated with, or reducing the incidence of, reducing the pathogenesis of, facilitating the recovery from or delaying the onset of) prostate cancer, breast cancer, endometrial cancer, hepatocellular cancer, lymphoma, multiple endocrine neoplasia, vaginal cancer, renal cancer, thyroid cancer, testicular cancer, leukemia, and ovarian cancer in a mammal in need thereof comprising the administration to said mammal of a compound selected from:

(R)-4-(1-(5-(4-fluorophenyl)-1,3,4-oxadiazol-2-yl)-2-hydroxy-2-methylpropylamino)-2-(trifluoromethyl)benzonitrile;

(R)-4-(1-(5-(4-fluorophenyl)-1,3,4-oxadiazol-2-yl)-2-hydroxy-2-methylpropylamino)-3-methyl-2-(trifluoromethyl)benzonitrile;

(R)-4-(1-(5-(4-cyanophenyl)-1,3,4-oxadiazol-2-yl)-2-hydroxy-2-methylpropylamino)-3-methyl-2-(trifluoromethyl)benzonitrile;

2-Chloro-4-((1R,2S)-1-(5-(4-cyanophenyl)-1,3,4-oxadiazol-2-yl)-2-hydroxypropylamino)-3-propylbenzonitrile;

(R)-2-chloro-4-(1-(5-(4-fluorophenyl)-1,3,4-oxadiazol-2-yl)-2-hydroxy-2-methylpropylamino)-3-methylbenzonitrile;

(R)-2-chloro-4-(1-(5-(4-cyanophenyl)-1,3,4-oxadiazol-2-yl)-2-hydroxy-2-methylpropylamino)-3-methylbenzonitrile; and 2-chloro-4-((1R,2S)-1-(5-(4-cyanophenyl)-1,3,4-oxadiazol-2-yl)-3,3,3-trifluoro-2-hydroxypropylamino)-3-methylbenzonitrile, or pharmaceutically acceptable salt of any of the foregoing or a pharmaceutical composition as described herein. In a particular embodiment, the mammal is a human.

The compounds of this invention may be present as solids and when so present, may be in an amorphous form or they may be crystalline. When the compounds of this invention are in the crystalline form, they might be present as a single polymorph or a mixture of polymorphs or even as a mixture of amorphous material together with one or more distinct polymorphs—the invention is not limited according to any particular solid or liquid state form.

The compounds of this invention contain at least one stereocenter and therefore, exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. Thus, "R" and "S" denote the relative configurations of substituents around one or more chiral carbon atoms. When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

The compounds of the invention may be prepared as individual isomers by incorporating or starting with a specific isomer, isomer-specific synthesis or resolution from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

Where compounds of this invention include one or more basic sites such as amines, acid addition salts can be made and this invention includes such acid addition salts. Some representative (non-limiting) acid addition salts include hydrochloride, hydrobromide, hydroiodide, acetate, benzenesulfonate, mesylate, besylate, benzoate, tosylate, citrate, tartrate, sulfate, bisulfate, lactate, maleate, mandelate, valerate, laurate, caprylate, propionate, succinate, phosphate, salicylate, napsylate, nitrate, tannate, resorcinate and the like, including multiprotic salts as well as mixtures of the acid addition salts. In cases where an amine is present, this invention also embraces quaternized ammonium salts of those amines. It should be appreciated that N-oxides of amines are also embraced within the definition of the compounds of this invention. Likewise, where compounds of this invention include one or more acid sites such as carboxylic acids, phenols and the like, basic addition salts can be made and this invention includes such basic addition salts. For example, some representative (non-limiting) acidic compounds of this invention may be present as their lithium, sodium, potassium, ammonium, trialkyammonium, calcium, magnesium, barium and the like.

The compounds of this invention can also be present as solvates and such solvates are embraced within the scope of this invention even where not explicitly described. Such solvates are preferably hydrates but can be solvates comprised of other solvents, preferably where those solvents are considered to be non-toxic or at least acceptable for administration to mammals, preferably humans. The solvates can be stoichiometric or non-stoichiometric, singular or in combination. Some exemplary solvates include water, ethanol, acetic acid and the like.

The therapeutic utility of these compounds includes "treating" a mammal, preferably a human where treating is understood to include treating, preventing, or ameliorating the symptoms associated with, or reducing the incidence of, reducing the pathogenesis of, facilitating the recovery from or delaying the onset of the syndrome, illness, malady or condition being considered. The compounds of this invention can also be useful in states or conditions where no clear deficit, illness or malady per se is perceived but rather, where a preferred condition, sensation, performance, capability or state is obtainable through therapeutic intervention with a compound of this invention.

The compounds of this invention, when used as therapeutics can be administered by any method known to one of skill in the art such as orally, bucally, intravenously, subcutaneously, intramuscularly, transdermally, intradermally, intravascularly, intranasally, sublingually, intracranially, rectally, intratumorally, intravaginally, intraperitonealy, pulmonary, ocularly and intratumorally.

As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

When administered, the compounds and compositions of this invention maybe given once daily or with multiple daily doses such as twice per day, three times per day and four times per day.

In one embodiment of this invention, the compound is administered orally where it can be formulated for solid dosage administration or liquid dosage administration. Solid dosage administration can be in the form of a tablet, granule, capsule, pill, pellet, powder and the like. Liquid dosage formulations include syrups, solutions, gels, suspensions, elixirs, emulsions, colloids, oils, and the like.

As mentioned previously, the compounds of this invention may be solids and when present as solids, they maybe of defined particle size. Where the compound of this invention is not particularly water soluble, it is sometimes preferable to administer the compound with a certain particle size—a particle size with a preferred range where the average mean particle size diameter is under 100 microns, or 75 microns, or 50 microns, or 35 microns, or 10 microns or 5 microns.

Solid dosage formulations will comprise at least one compound of this invention together with one or more pharmaceutical excipients. Those excipients are known to one of skill in the art and include, by way of non-limiting example diluents (monosaccharides, disaccharides and polyhydric alcohols including starch, mannitol, dextrose, sucrose, microcrystalline cellulose, maltodextrin, sorbitol, xylitol, fructose and the like), binders (starch, gelatin, natural sugars, gums, waxes and the like), disintegrants (alginic acid, carboxymethylcellulose (calcium or sodium), cellulose, crocarmellose, crospovidone, microcrystalline cellulose, sodium starch glycolate, agar and the like), acidic or basic buffering agents (citrates, phoshphates, gluconates, acetates, carbonates, bicarbonates and the like), chelating agents (edetic acid, edetate calcium, edetate disodium and the like), preservatives (benzoic acid, chlorhexidine gluconate, potassium benzoate, potassium sorbate, sorbic acid, sodium benzoate and the like), glidants and lubricants (calcium stearate, oils, magnesium stearate, magnesium trisilicate, sodium fumarate, colloidal silica, zinc stearate, sodium oleate, stearic acid, and the like), antioxidants and/or preservatives (tocopherols, ascorabtes, phenols, and the like) and acidifying agents (citric acid, fumaric acid, malic acid, tartaric acid and the like) as well as coloring agents, coating agents, flavoring agents, suspending agents, dessicants, humectants and other excipients known to those of skill in the art.

The solid dosage formulations of this invention can be prepared in different forms including most commonly, tablets and capsules. The tablets can be formulated by a wide variety of methods known to one of skill in the art including, for example, preparing a dry powder mixture of the drug substance in combination with one or more of the excipients granulating the mixture and pressing to together into a tablet and optionally coating the tablet with an enteric or non-enteric coating. The final coat typically includes a light protective pigment such as titanium oxide and a shellac or wax to keep the tablet dry and stable. While not intending to be limited by theory or example, in some instances it might be preferred to prepare the tablets by wet granulating the drug with one or more of the excipients and then extruding the granulated material.

The solid dosage forms of this invention also include capsules wherein the drug is enclosed inside the capsule either as a powder together with optional excipients or as granules containing usually including one or more excipients together with the drug and wherein the granule in turn can be optionally coated, for example, enterically or non-enterically.

In certain embodiments of this invention, the solid dosage formulations of this invention are formulated in a sustained release formulation. Such formulations are known to those of skill in the art and generally rely on the co-formulation of the drug with one or more matrix forming substances that slow the release of the androgen receptor modulator thus extending the compound's lifetime in the digestive track and thereby extend the compounds half-life. Some non-limiting matrix forming substances include hydroxypropyl methylcellulose, carbopol, sodium carboxymethylcellulose and the like.

In some embodiments of this invention, the compounds are formulated for delivery other than via a solid oral dosage form. For example, in certain instances it might be preferable to deliver a compound of this invention by a pulmonary route. A pulmonary route of administration typically means that the compound of this invention is inhaled into the lung where it is absorbed into the circulation. Such a route of administration has the advantage of avoiding a first pass liver effect thereby possibly increasing bioavailability as well as decreasing or eliminating undesirable androgen agonist effects on the liver such as increasing liver enzymes and/or decreasing HDL. Formulating a compound of the invention for pulmonary delivery can be accomplished by micronizing the compound of the invention to a very fine size particle, typically with a mean average diameter of less than 20 microns, or less than 10 microns or between 2 and 5 microns. The powder may then be inhaled by itself or more likely mixed with one or more excipients such as lactose or maltose. The powder can then be inhaled in a dry powder inhaling device either once or multiple times per day depending on the particular compound and the patients need. Other types of pulmonary dosage forms are also embraced by this invention. In an alternative to the dry powder delivery, the compound of this invention may be suspended in an aerosolizing medium and inhaled as a suspension through a meter dosed inhaler or a nebulizer.

The compounds of this invention can be formulated for transdermal delivery. Effective advantage of these compounds can be taken through a wide variety of transdermal options. For example, the compounds of this invention maybe formulated for passive diffusion patches where they are preferably embedded in a matrix that allows for slow diffusion of the compound into the treated subject's circulation. For this purpose, the compound is preferably dissolved or suspended in solvents including by way of non-limiting examples one or more of ethanol, water, propylene glycol, and Klucel HF. In some instances, a polymer matrix (e.g. acrylate adhesive) will comprise the bulk of the transdermal formulation. In some instances, the transdermal formulations maybe designed to be compatible with alternate transdermal delivery technologies. For example, some transdermal technologies achieve greater and/or more consistent delivery by creating micropores in the skin using radio frequency, heat, ultrasound or electricity. In some cases, the compounds of this invention can be used with microneedle technology wherein the compound is loaded into very small needles which due not need to penetrate the dermis to be effective.

The compounds of this invention may be employed alone or in combination with other therapeutic agents. By way of non-limiting example, the compounds of this invention can be used in combination with anti-lipidemics (statins, fibrates, omega-3 oils, niacinates and the like), bone anti-resorptives (bisphosphonates, estrogens, selective estrogen receptor modulators (SERMs), calcitonin, and the like), bone anabolic agents (PTH and fragments e.g teriparatide, PTHRP and analogues e.g. BaO58), anti-diabetics (e.g. insulin sensitizers, glucose absorption and synthesis inhibitors (e.g. metformin)), anti-anxiety agents, antidepressants, anti-obesity agents, contraceptive agents, anti-cancer agents, PPARγ agonists (e.g. pioglitazone), and the like. When used in combination, the compounds of this invention may be co-formulated or co-administered wherein said co-administration does not require dosing at exactly the same time but rather indicates that the patient is undergoing treatment with one or more of the additional agents during the timeframe of treatment with the selective androgen modulators of this invention. Thus, the additional drug(s) for combination treatment can be administered concomitantly, sequentially or separately from the compounds of this invention.

The compounds of this invention may be administered according to different dosage scheduling and the dosage may be adjusted as deemed necessary by the subject or preferably by the subject in consultation with a qualified practitioner of medicine. Dosing of the compounds of this invention can take place by multiple routes and consequently, the dosing schedule and amounts are dependent not only on the particular subject's weight, sex, age, therapy contemplated, etc but also by the route of the drug chosen.

By way of non-limiting example, the compounds of this invention may be dosed by the oral route in a once daily, twice daily, three times daily or more than three times per day depending on the particular needs of that subject, the formulation of the drug, etc. The dosage will typically be from about 0.01 mg to 500 mg of drug per daily dosage, for example from about 0.1 mg to about 10 mg, such as from about 0.1 mg to about 3 mg, or from about 0.1 mg to about 250 mg of drug per daily dosage, or from about 1 mg to about 150 mg of drug per daily dosage, or from about 5 mg to about 100 mg of drug per daily dosage.

It is understood that the amount of compound dosed per day can be administered every day, every other day, every 2 days, every 3 days, every 4 days, every 5 days, etc. For example, with every other day administration, a 5 mg per day dose can be initiated on Monday with a first subsequent 5 mg per day dose administered on Wednesday, a second subsequent 5 mg per day dose administered on Friday, etc. In one embodiment, a compound of this invention is dosed once every seven days.

The compounds of this invention can also be dosed on a monthly basis meaning that administration is done once per month. In addition, the compounds of this invention can be dosed on a weekly basis (once a week), every other week, every three weeks or every four weeks for a single day or multiple days.

The compounds of this invention can also be dosed on an as needed or "pro re nata" "prn" schedule, and "on demand". In this type of dosing, the compounds of this invention are administered in a therapeutically effective dose at some time prior to commencement of an activity wherein the therapeutic effect of the compounds of this invention is desirable. Administration can be immediately prior to such an activity, including about 0 minutes, about 10 minutes, about 20 minutes, about 30 minutes, about 1 hour, about 2 hours, about 3 hours, about 4 hours, about 5 hours, about 6 hours, about 7 hours, about 8 hours, about 9 hours, or about 10 hours prior to such an activity, depending on the formulation.

The compounds of this invention can be prepared by a variety of synthetic routes and techniques known to those of skill in the art. The processes disclosed herein should not be construed as limiting the examples or scope of the invention in any way but rather are provided as just some of the representative ways that the compounds of this invention can be or were prepared.

In some cases, protective groups are employed in the synthesis of the compounds of this invention and it should be appreciated that there are a diverse array of protective groups and strategies that can be employed in organic synthesis (T. W. Green and P. G. M. Wuts (2006) Greene's Protective Groups in Organic Synthesis, herein incorporated by reference in its entirety) and that where a specific protective group is referred to, any appropriate protective group should be considered.

In some instances, leaving groups are employed in the synthesis of compounds of this invention. Where a specific leaving group is referred to, it should be appreciated that other leaving groups might also be used. Leaving groups typically include those groups that can stabilize an anion. In the case of nucleophilic aromatic substitutions, the leaving group may be an anion or a neutrally charged group. In some cases, the leaving group for nucleophilic aromatic substitution may be a group that is not typically considered to be a stabilized anion (e.g. fluoride or hydride). While not intending to be bound by theory or the examples, some typical nucleophilic leaving groups include halogens, sulfonates (O-mesylates, O-tosylates, etc), hydrides, quaternized amines, nitro, and the like. Additional discussion and examples can be found in leading textbooks on organic chemistry including, for example, March's Advanced Organic Chemistry: Reactions, Mechanisms, and Structure, 5$^{th}$ Edition, which is herein incorporated in its entirety.

In scheme 1, a general method for preparing the compounds of this invention is set forth. In scheme 1, the starting material used is a phenyl ring substituted with a leaving group where that leaving group is typically a halogen, preferably a fluorine but may also be additional leaving groups such as trialkylammonium salts and the like. The group displacing the leaving group is an amine compound of formula B. The amines can be prepared by different methods well-known by those of skill in the art and in many cases, the amines are commercially available hydroxyl-amino acids (e.g. D-threonine, D-serine, D-allo-threonine, etc). Normally, the reaction is done in the presence of a base to facilitate the displacement. Inorganic bases such as $K_2CO_3$, $Na_2CO_3$, NaH, etc can typically be used to good effect, or in some cases organic bases might be preferable ($Et_3N$, etc) depending on the solvent, reactants, etc. Normally, a solvent is chosen that can dissolve at least some of each of the components of the reaction. Polar solvents are generally preferred since they help facilitate the dissolution of one or more of the components as well as can accelerate nucleophilic substitution reactions. DMSO can be a very good solvent for these reactions but other solvents such as alcohols, DMF, HMPA, etc. should be considered as well. After the addition reaction, the product C is isolated and carried to the next step. Isolation techniques are well-known to those of skill in the art and include chromatography and/or crystallization. In cases where $R_3$ is hydrogen, one can optionally protect the alcohol at this point prior to the hydrazide coupling if a free alcohol interferes substantially in the coupling. After the formation of the coupled product, the bis-acyl hydrazide product can be dehydrated using a number of potential reagents well-known to those of skill in the art. Some possibly useful reagents include triphenylphosphine, polymer supported triphenylphosphine, $Cl_2$, $Br_2$, $I_2$, $CCl_3CN$; $ClCH_2CH_2Cl$, $BrCH_2CH_2Br$, $CCl_4$, $CBr_4$, $CI_4$, $Cl(CO)(CO)Cl$, $POCL_3$, $PCl_5$, $SOCl_2$, $H_2SO_4$, HCl, $H_3PO_4$, $O(SO_2CF_3)_2$, TMS-polyphosphate, $MeOC(=O)N^-SO_2N^+Et_3$ (Burgess reagent), diazophosphorene, toluenesulfonyl chloride, $CH_3SO_2Cl$, $CF_3SO_2Cl$, $P_2O_5$, $Me_2^+N=CH-OPCl_2$, Lawesson's reagent, 2-tert-Butylimino-2-diethylamino-1,3-dimethylperhydro-1,3,2-diazaphosphorine, polystyrene-supported 2-tert-Butylimino-2-diethylamino-1,3-dimethylperhydro-1,3,2-diazaphosphorine, and $(Me_3Si)_2NH$. It is often preferable to protect the alcohol ($R_3$=hydrogen), prior to the dehydration. Some protection groups that have been found to be particularly useful include trialkyl silyl groups (e.g. TBDMS) but other groups such as esters, ethers, etc. could be useful as well. Protecting groups might also be considered at other positions of the molecule depending on the compound structure and likelihood of interference of that group during any point in the synthesis. After the dehydration to form the oxadiazole, additional manipulations can take place such as de-protecting, making a salt, or converting one of the variable groups to a different group.

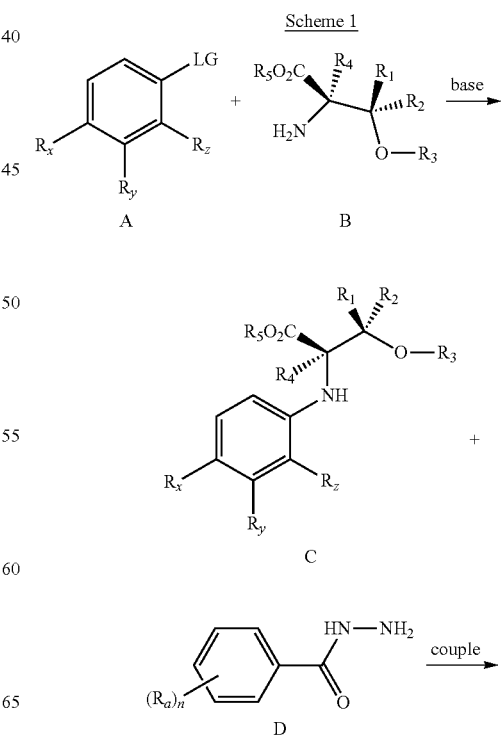

Scheme 1 diacylhydrazide E can then be taken onto the final product G as demonstrated previously in scheme 1.

Scheme 1a

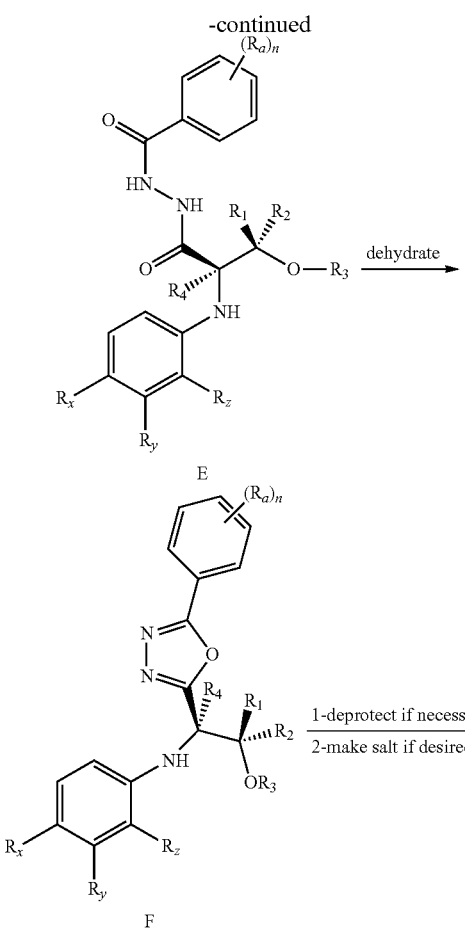

E

F

G

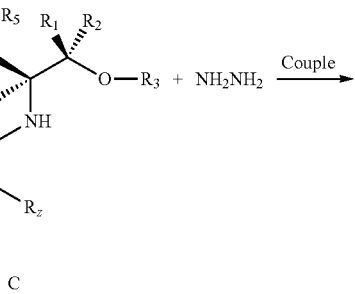

C

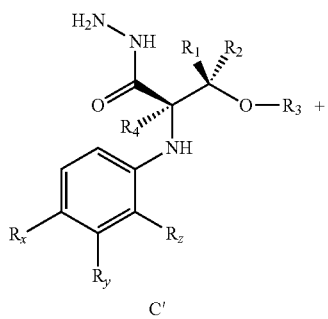

C'

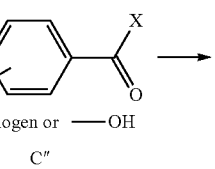

C''

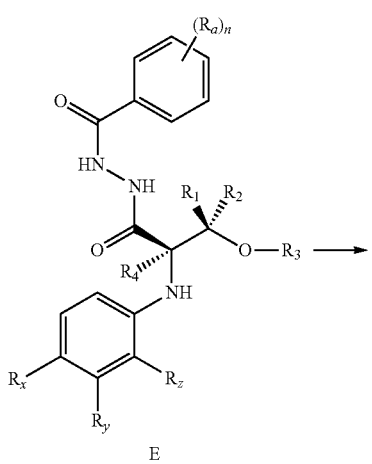

E $R_x$ is e.g, CN; $R_y$ is e.g., $CF_3$ or Cl; $R_z$ is e.g., H, $C_{1-3}$ alkyl; $R_a$ is e.g., CN or F n is 1; $R_1$ and $R_2$ are each independently selected from e.g, hydrogen, $CH_3$ or $CF_3$; $R_3$ is e.g., hydrogen, Bn or TBS; and $R_5$ is hydrogen.

Alternatively, compounds of formula G from scheme 1 might be prepared by the alternative route illustrated in scheme 1a. In the alternative route, the acyl hydrazide used in making the diacyl hydrazide precursor to the 1,3,4-oxadiazole is present on the core portion of the molecule rather than on the phenacyl portion. Where $R_5$ is hydrogen, the acyl hydrazide C' can be prepared by a coupling reaction between the carboxylic acid and hydrazine using standard coupling reaction conditions known to those of skill in the art. The -continued

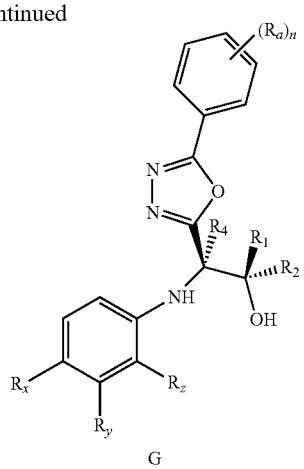

G

Determination of Biological Activity

In order to demonstrate the utility of the compounds of this invention, an androgen receptor binding assay was performed wherein many of the compounds of this invention are shown to demonstrate significant affinity for the androgen receptor. The assay was performed as specified by the manufacturer (Invitrogen, Madison, Wis.). Briefly, 1 µl of 10 mM compound was added to 500 µl of AR screening buffer in a 1.5 ml eppendorf tube to make a $2\times10^{-5}$M stock. 10-fold serial dilutions of the test compounds were prepared ranging in concentration from $10^{-5}$M to $10^{-12}$M. Each dilution was added in triplicate to a black 384-microtiter plate. The test compounds will be diluted 2-fold in the final reaction. 2×AR-Fluormone™ complex was prepared with 2 nM Flourmone AL Green™ and 30 nM AR. 25 µl of 2× complex was aliquoted to each reaction well, such that the final reaction volume was 50 µl per well. Plate was sealed with a foil cover and incubated in the dark at room temperature for 4 h. Polarization values for each well were measured. The polarization values were plotted against the concentration of the test compound. The concentration of the test compound that results in half-maximum shift equals the $IC_{50}$ of the test compound. As a control, a competition curve for R1881 (methyltrienolone) was performed for each assay. Curve Fitting was performed using GraphPad Prism® software from GraphPad™ Software Inc. Binding data are reported as a single determination if the experiment was run once only and as the average of experiments if the binding experiment was performed two or more times with that compound. Results are set forth in Table 1.

In Vivo Rat Model of Androgen and Anabolic Activity-Rat Herschberger Assay

The following is a typical procedure of the in vivo evaluation of the selective androgens of this invention. In particular, this assay looks primarily at the ability of the selective androgens of this invention to increase muscle size in an immature, castrated rat. In addition, androgenic effects are looked at primarily by weighing the prostate and seminal vesicles. Selective compounds will show a greater increase in the levator ani relative to the prostate and seminal vesicles when compared to testosterone treated, castrated animals or to intact animals that have not been treated. Immature Sprague Dawley male rats were obtained Charles River Laboratories (Stoneridge, N.Y.). All animals were maintained in a temperature and humidity controlled room with a 12 hr light: 12 hr dark cycle, with ad lib access to food (TD 291615, Teklad, Madison, Wis.) and water. Rats were anesthetized and orchidectomized (GDX) or sham surgery (SHAM) was performed. After a 7-day recovery period, the animals were randomized according to weight and assigned to treatment groups (n=5), SHAM, OVX+vehicle, OVX+Cpd treated. Testosterone propionate (TP 1 mg/kg in 5% DMSO/95% corn oil) was administered by once daily subcutaneous injections, while the compounds of the invention were dosed in vehicle (typically 20% cyclodextrin or 0.5% carboxymethylcellulose) was administered by once daily oral gavage. The rats were then dosed once daily for 4 days. All animals were euthanized via carbon dioxide inhalation 24 hs after the last dose. The prostate, seminal vesicle and levator ani and bulba cavernous (LABC) tissues were removed, weighed and recorded. Body weights were recorded for each animal at baseline and at sacrifice. Results are set forth in the FIGURE.

In Vivo Models of Bone Loss and Prevention

Compounds of this invention may also be assayed in vivo to determine their effect on preventing bone loss in animal models of bone loss. Animal models of bone loss are well-known to those of ordinary skill in the art. Examples of bone loss models include the rat and mouse ovariectomized models. Examples of such models are replete in the art, some non-limiting methods and examples are provided in Cesnjaj, et al *European Journal of Clinical Chemistry and Clinical Biochemistry* (1991), 29(4), 211-219; Y. L. Ma et al., *Japanese Journal of Bone and Mineral Research* 23 (Suppl.):62-68 (2005); Ornoy, et al, Osteoporosis: Animal Models for the Human Disease; *Animal Models of Human Related calcium Metabolic Disorders* (1995), 105-126.

Compound Characterization

All solvents were commercially available and used without further purification. Reactions were monitored by thin-layer chromatography (TLC) on silica gel plates (60 F254; EMD Chemicals) which were visualized using ultraviolet light, iodine vapor, or vanillin stain. Flash chromatography was performed on silica gel (230-400 mesh, Silicycle) using commercially available high purity solvents. $^1$H and $^{13}$C NMR spectra were determined in $CDCl_3$, MeOH-$d_6$, DMSO-$d_6$, or acetone-$d_6$ using either a Varian Unity 400 MHz spectrometer or a Varian Unity 500 MHz spectrometer. Proton chemical shifts (δ) are relative to the residual solvent peaks for each deuterated solvent and expressed in ppm. Coupling constants (J) are expressed in hertz. Mass spectra were obtained on a Waters HQH Quattro II mass spectrometer. All melting points were obtained on a Tottoli melting point apparatus manufactured by Büchi and are uncorrected. All hydrazides were either purchased or prepared according to procedures described in the literature. All chemical reagents are commercially available and were used without further purification unless stated otherwise.

Example 1

(R)-4-(1-(5-(4-fluorophenyl)-1,3,4-oxadiazol-2-yl)-2-hydroxy-2-methylpropylamino)-2-(trifluoromethyl)benzonitrile

Intermediate 1a

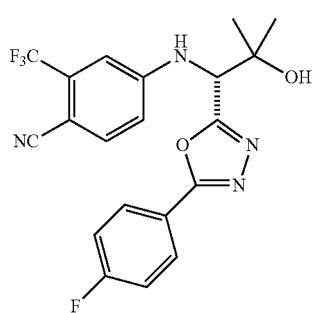

(R)-2-(4-cyano-3-(trifluoromethyl)phenylamino)-3,3-dimethylbutanoic acid

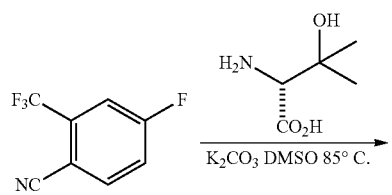

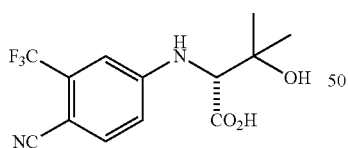

4-fluoro-2-(trifluoromethyl)benzonitrile (7.10 g, 37.55 mmol) was mixed together with (R)-2-amino-3-hydroxy-3-methylbutanoic acid (5 g, 37.55 mmol) in DMSO (220 mL). K$_2$CO$_3$ (15.57 g, 112.65 mmol) was added to the reaction mixture and the reaction mixture stirred at 85° C. for 96 h. The reaction mixture was allowed to cool to room temperature and quenched with H$_2$O (40 mL) and extracted with EtOAc (2×80 mL). The aqueous layer was then acidified with solid citric acid and extracted with EtOAc (2×80 mL). The later organic extracts were combined, washed with H$_2$O (2×30 mL), dried (Na$_2$SO$_4$), filtered and concentrated under reduced pressure to provided the title compound as a pale yellow solid (11.1 g, 98%): $^1$H NMR (400 MHz, d$_6$-acetone, δ in ppm) 7.57 (d, J=9 Hz, 1H), 6.98 (d, J=2 Hz, 1H), 6.80 (dd, J=9 and 2 Hz, 1H), 5.52 (br s, 1H), 3.96 (d, J=7 Hz, 1H), 1.42 (s, 3H), and 1.36 (s, 3H).

Intermediate 1b

(R)-4-cyano-N'-(2-(4-cyano-3-(trifluoromethyl)phenylamino)-3-hydroxy-3-methylbutanoyl)benzohydrazide

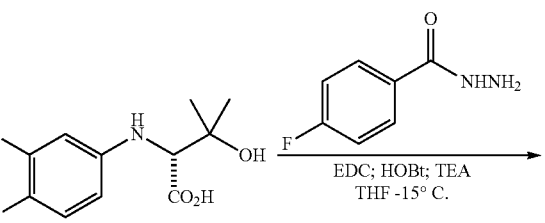

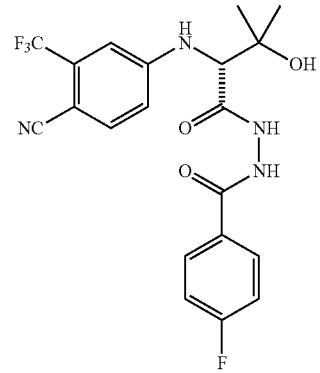

(R)-2-(3-chloro-4-cyano-2-methylphenylamino)-3-hydroxy-3-methylbutanoic acid (6.8 g, 22.49 mmol) and 4-fluorobenzohydrazide (3.82 g, 24.75 mmol) were mixed together in THF (200 ml) and cooled to −15° C. under N$_2$ atmosphere. To the pre-cooled reaction mixture were added hydroxybenzotriazole (HOBT) (3.04 g, 22.49 mmol), TEA (4.7 mL, 33.74 mmol) followed by N-(3-Dimethylaminopropyl)-N'-ethylcarbodiimide hydrochloride (EDCI) (6.47 g, 33.74 mmol). The reaction mixture was allowed to stir at −20° C. for 20 min and then at room temperature overnight. After the reaction was complete ethyl acetate (70 mL) was added and the solution was washed with 5% citric acid (2×40 mL), 5% NaHCO$_3$ (2×40 mL) followed by water (40 mL) and then dried (Na$_2$SO$_4$) to provide the crude product as a yellow solid (9.32 g, 95%): $^1$H NMR (400 MHz, d$_6$-acetone, δ in ppm) 9.61 (br s, 1H), 8.03-7.97 (m, 2H), 7.72 (d, J=9 Hz, 1H), 7.35

(d, J=2 Hz, 1H), 7.08 (dd, J=9 and 2 Hz, 1H), 6.56 (d, J=9 Hz, 1H), 4.19 (d, J=9 Hz, 1H), 1.42 (s, 3H) and 1.38 (s, 3H).

Example 1

(R)-4-(1-(5-(4-fluorophenyl)-1,3,4-oxadiazol-2-yl)-2-hydroxy-2-methylpropylamino)-2-(trifluoromethyl)benzonitrile

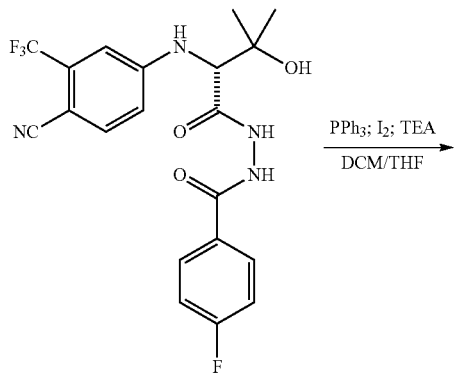

Triphenylphosphine (249 mg, 0.95 mmol) was dissolved in DCM (100 mL) followed by addition of I₂ (241 mg, 0.94 mmol) and TEA (0.26 mL, 238.92 mmol) at 0° C. (R)-4-chloro-N-(2-(3-chloro-4-cyano-2-methylphenylamino)-3-hydroxy-3-methylbutanoyl)benzohydrazide (208 mg, 0.47 mmol) in DCM (10 mL) and THF (5 mL) was added to the pre-cooled solution mixture of PPh₃/I₂/TEA system and stirred for 30 min. The reaction mixture was then concentrated to furnish a yellow solid (781 mg). The crude material was chromatographed with EtOAc:Hexanes (2:1) to furnish the title compound as a white solid (100 mg). ¹H NMR (500 MHz, Acetone d₆, δ in ppm): 8.01-7.79 (m, 2H), 7.58 (d, J=9

Hz, 1H), 7.18 (t, J=8 Hz, 1H), 7.04 (d, J=2 Hz, 1H), 6.84 (dd, J=9 and 2 Hz, 1H), 5.55 (d, J=9 Hz, 1H), 4.73 (d, J=9 Hz, 1H), 1.49 (s, 3H) and 1.35 (s, 3H).

Example 2

(R)-4-(1-(5-(4-fluorophenyl)-1,3,4-oxadiazol-2-yl)-2-hydroxy-2-methylpropylamino)-3-methyl-2-(trifluoromethyl)benzonitrile Intermediate 2a

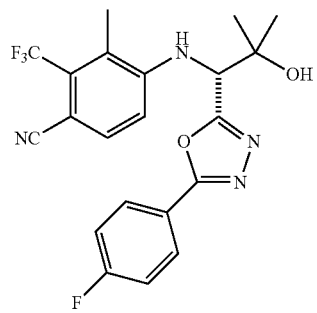

(R)-2-(4-cyano-2-methyl-3-(trifluoromethyl)phenylamino)-3-hydroxy-3-methylbutanoic acid

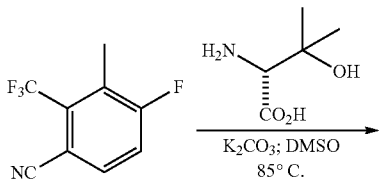

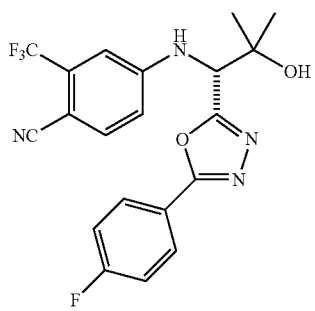

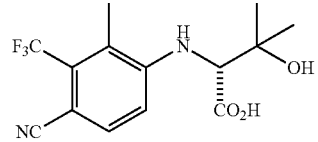

4-fluoro-3-methyl-2-(trifluoromethyl)benzonitrile (763 mg, 3.76 mmol) was mixed together with (R)-2-amino-3-hydroxy-3-methylbutanoic acid (500 mg, 3.76 mmol) in DMSO (25 mL). K₂CO₃ (1.56 g, 11.28 mmol) was added to the reaction mixture and the reaction mixture stirred at 85° C. for 18 h. The reaction mixture was allowed to cool to room temperature, quenched with H₂O (25 mL) and extracted with EtOAc (2×30 mL). The aqueous layer was then acidified with solid citric acid and extracted with EtOAc (2×80 mL). The later organic extracts were combined, washed with H₂O (2×30 mL), dried (Na₂SO₄), filtered and concentrated under reduced pressure to provided the title compound as a yellow solid (1.15 g, 97%): ¹H NMR (400 MHz, d₆-acetone, δ in ppm) 7.63 (d, J=9 Hz, 1H), 6.97 (d, J=9 Hz, 1H), 5.62 (d, J=9 Hz, 1H), 4.20 (d, J=9 Hz, 1H), 2.33 (s, 3H), 1.43 (s, 3H) and 1.42 (s, 3H).

Intermediate 2b (R)—N'-(2-(4-cyano-2-methyl-3-(trifluoromethyl) phenylamino)-3-hydroxy-3-methylbutanoyl)-4-fluorobenzohydrazide 2H), 7.69-7.63 (m, 1H), 7.27-7.21 (m, 2H), 7.01-6.95 (m, 1H), 5.54 (d, J=7 Hz, 1H), 4.14 (d, J=8 Hz, 1H), 2.38 (s, 3H), 1.47 (s, 3H) and 1.43 (s, 3H).

Example 2

(R)-4-(1-(5-(4-fluorophenyl)-1,3,4-oxadiazol-2-yl)-2-hydroxy-2-methylpropylamino)-3-methyl-2-(trifluoromethyl)benzonitrile

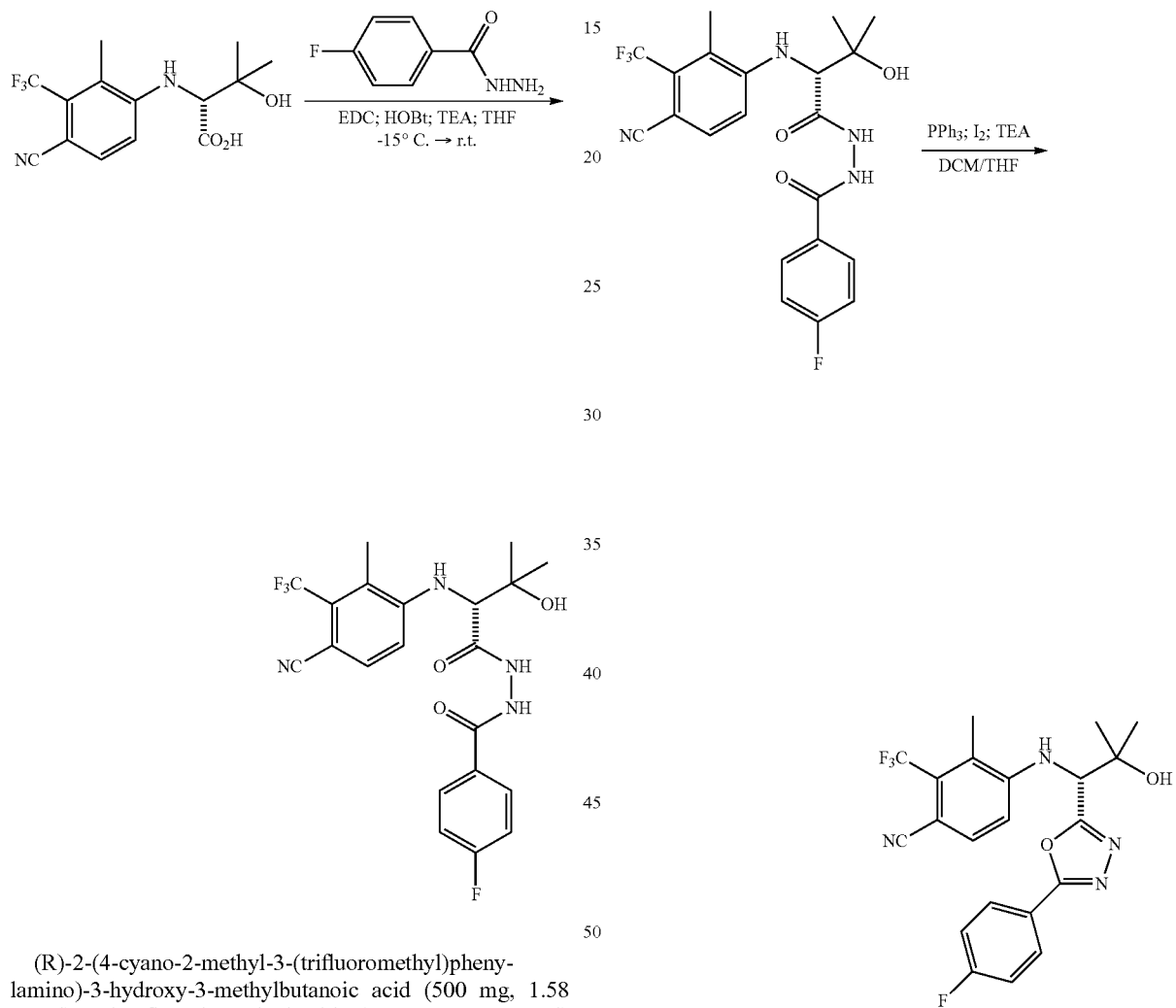

(R)-2-(4-cyano-2-methyl-3-(trifluoromethyl)phenylamino)-3-hydroxy-3-methylbutanoic acid (500 mg, 1.58 mmol) and 4-fluorobenzohydrazide (244 mg, 1.58 mmol) were mixed together in THF (20 mL) and cooled to −15° C. under N₂ atmosphere. To the pre-cooled reaction mixture were added hydroxybenzotriazole (HOBT) (214 mg, 1.58 mmol), TEA (0.33 mL, 2.37 mmol) followed by N-(3-Dimethylaminopropyl)-N'-ethylcarbodiimide hydrochloride (EDCI) (454 mg, 2.37 mmol). The reaction mixture was allowed to stir at −20° C. for 20 min and then at room temperature overnight. After the reaction was complete, ethyl acetate (50 mL) was added and the solution was washed with 5% citric acid (2×40 mL), 5% NaHCO₃ (2×40 mL) followed by water (40 mL) and then dried (Na₂SO₄) to provide the crude product as a yellow solid (660 mg, 92%): ¹H NMR (400 MHz, d₆-acetone, δ in ppm) 9.81 (br s, 1H), 8.02-7.95 (m, Triphenylphosphine (766 mg, 2.92 mmol) was dissolved in DCM (100 mL) followed by addition of I₂ (741 mg, 2.92 mmol) and TEA (0.81 mL, 5.84 mmol) at 0° C. (R)—N'-(2-(4-cyano-2-methyl-3-(trifluoromethyl)phenylamino)-3-hydroxy-3-methylbutanoyl)-4-fluorobenzohydrazide (660 mg, 1.46 mmol) in DCM (20 mL) and THF (10 mL) was added to the pre-cooled solution mixture of PPh₃/I₂/TEA system and stirred for 30 min. The reaction mixture was then concentrated to furnish a yellow solid (781 mg). The crude material was chromatographed with EtOAc:Hexanes (2:1) to furnish the title compound as a white solid (361 mg, 57%). ¹H NMR (500 MHz, Acetone d₆, δ in ppm): 7.97-7.94 (m, 2H), 7.49 (d, J=9 Hz, 1H), 7.19-7.14 (m, 2H), 6.81 (d, J=9 Hz, 1H), 5.55 (d, J=9 Hz, 1H), 4.72 (d, J=9 Hz, 1H), 2.35 (s, 3H), 1.50 (s, 3H) and 1.35.

Example 3

(R)-4-(1-(5-(4-cyanophenyl)-1,3,4-oxadiazol-2-yl)-2-hydroxy-2-methylpropylamino)-3-methyl-2-(trifluoromethyl)benzonitrile

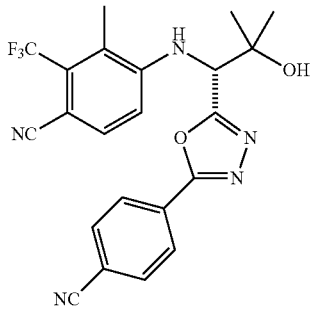 [SMILES: Cc1c(N[C@@H](c2nnc(-c3ccc(C#N)cc3)o2)C(C)(C)O)ccc(C#N)c1C(F)(F)F]

Intermediate 3a (R)-4-cyano-N'-(2-(4-cyano-2-methyl-3-(trifluoromethyl)phenylamino)-3-hydroxy-3-methylbutanoyl)benzohydrazide

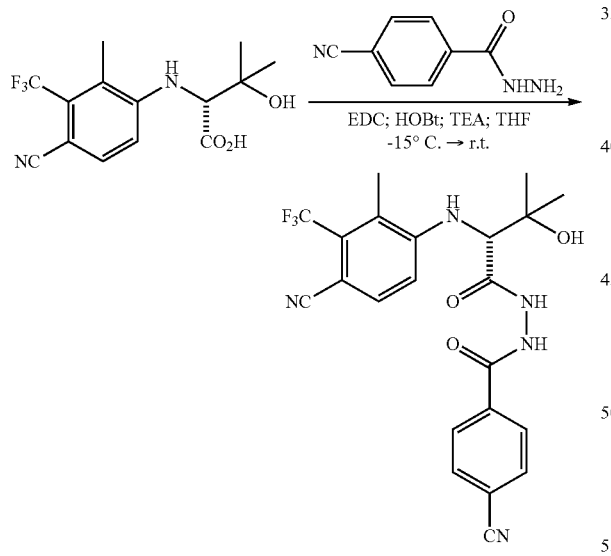

(R)-2-(4-cyano-2-methyl-3-(trifluoromethyl)phenylamino)-3-hydroxy-3-methylbutanoic acid (500 mg, 1.58 mmol) and 4-cyanobenzohydrazide (301 mg, 1.87 mmol) were mixed together in THF (20 mL) and cooled to −15° C. under N$_2$ atmosphere. To the pre-cooled reaction mixture were added hydroxybenzotriazole (HOBT) (230 mg, 1.70 mmol), TEA (0.36 mL, 2.55 mmol) followed by N-(3-Dimethylaminopropyl)-N'-ethylcarbodiimide hydrochloride (EDCI) (489 mg, 2.55 mmol). The reaction mixture was allowed to stir at −20° C. for 20 min and then at room temperature overnight. After the reaction was complete, ethyl acetate (50 mL) was added and the solution was washed with 5% citric acid (2×40 mL), 5% NaHCO$_3$ (2×40 mL) followed by water (40 mL) and then dried (Na$_2$SO$_4$) to provide the crude product as a yellow solid (790 mg, 99%): $^1$H NMR (400 MHz, d$_6$-acetone, δ in ppm) 9.92 (br s, 1H), 9.49 (br s, 1H), 7.99 (d, J=9 Hz, 2H), 7.81 (d, J=9 Hz, 2H), 7.42 (d, J=9 Hz, 1H), 6.61 (d, J=9 Hz, 1H), 6.53 (dd, J=12 and 18 Hz, 1H), 5.99 (d, J=9 Hz, 1H), 5.73 (dd, J=2 and 12 Hz, 2H), 5.64 (dd, J=2 and 18 Hz), 4.29-4.22 (m, 1H), 4.01-3.99 (m, 1H) and 1.20 (d, J=7 Hz, 3H).

Example 3

(R)-4-(1-(5-(4-cyanophenyl)-1,3,4-oxadiazol-2-yl)-2-hydroxy-2-methylpropylamino)-3-methyl-2-(trifluoromethyl)benzonitrile

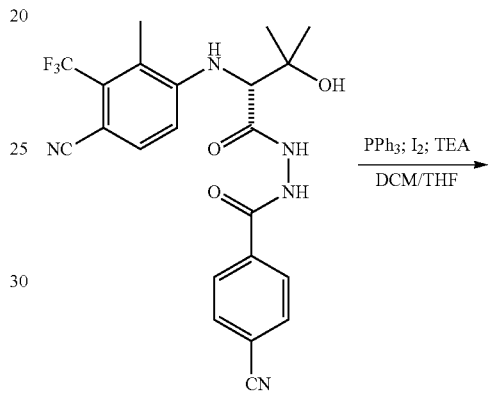

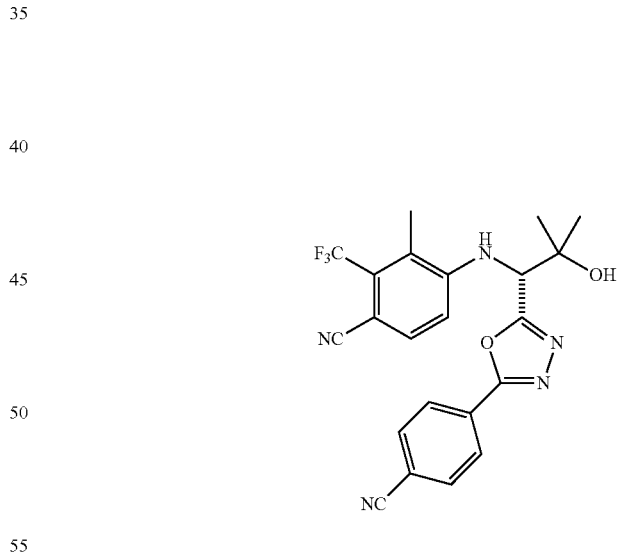

Triphenylphosphine (766 mg, 2.92 mmol) was dissolved in DCM (100 mL) followed by addition of I$_2$ (741 mg, 2.92 mmol) and TEA (0.81 mL, 5.84 mmol) at 0° C. (R)—N'-(2-(4-cyano-2-methyl-3-(trifluoromethyl)phenylamino)-3-hydroxy-3-methylbutanoyl)-4-fluorobenzohydrazide (660 mg, 1.46 mmol) in DCM (20 mL) and THF (10 mL) was added to the pre-cooled solution mixture of PPh$_3$/I$_2$/TEA system and stirred for 30 min. The reaction mixture was then concentrated to furnish a yellow solid (781 mg). The crude material was chromatographed with EtOAc:Hexanes (2:1) to furnish the title compound as a white solid (361 mg, 57%). $^1$H NMR (500 MHz, Acetone d$_6$, δ in ppm): 8.08 (d, J=9 Hz, 2H), 7.91

(d, J=9 Hz, 2H), 7.70-7.64 (m, 1H), 7.02-6.95 (m, 1H), 6.64 (d, J=8 Hz, 1H), 4.14 (d, J=9 Hz, 1H), 2.38 (br s, 1H), 1.48 (s, 3H) and 1.44 (s, 3H).

Example 4

2-Chloro-4-((1R,2S)-1-(5-(4-cyanophenyl)-1,3,4-oxadiazol-2-yl)-2-hydroxypropylamino)-3-pronyl-benzonitrile

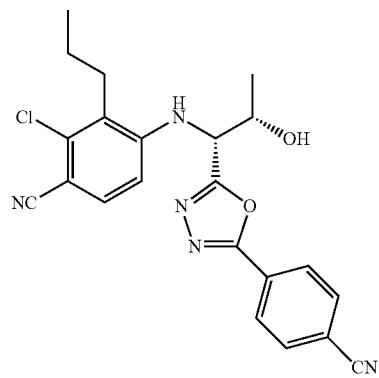 [SMILES: CCCc1c(N[C@@H](c2nnc(-c3ccc(C#N)cc3)o2)[C@H](C)O)ccc(C#N)c1Cl]

Intermediate 4a (2R,3S)-2-(3-Chloro-4-cyano-2-propylphenylamino)-3-hydroxybutanoic acid

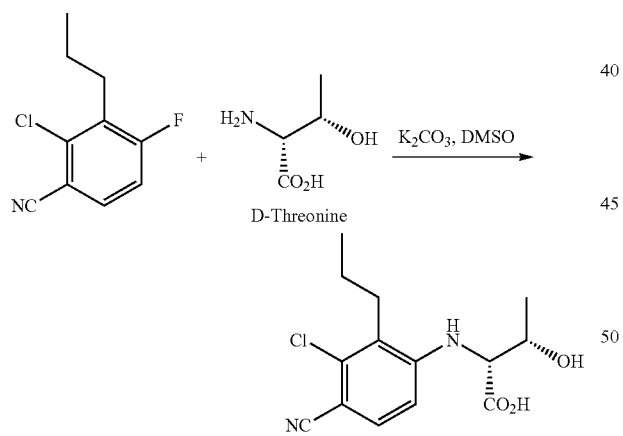

2-Chloro-4-fluoro-3-propylbenzonitrile (CAS 924626-89-1, 3.22 g, 16.3 mmol) was mixed together with H-D-Thr-OH (2.33 g, 19.6 mmol) in DMSO (30 mL) at room temperature. K$_2$CO$_3$ (4.73 g, 34.2 mmol) was added and the reaction mixture was stirred at 80° C. for 40 h. The reaction mixture was then cooled to room temperature and partitioned between water and EtOAc. The layers were separated and the aqueous extract was washed once with EtOAc. The aqueous extract was then acidified by slow addition of citric acid and stirred for 10 min at room temperature. The solution was extracted with EtOAc several times and the organic extracts were combined, washed with water, dried over Na$_2$SO$_4$, filtered, and concentrated in vacuo to obtain the crude product (0.650 g, 13% yield), which was carried on to the next step without further purification.

Intermediate 4b

N'-((2R,3S)-2-(3-Chloro-4-cyano-2-propylphenylamino)-3-hydroxybutanoyl)-4-cyanobenzohydrazide

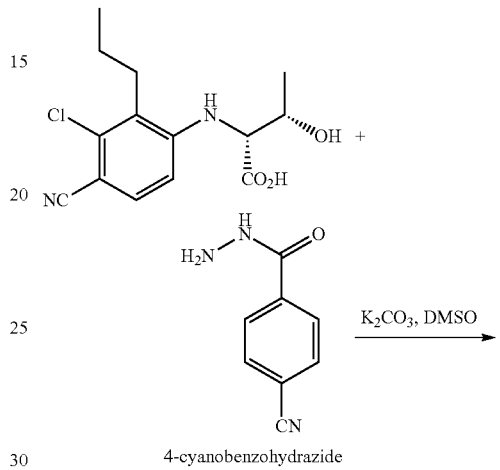

(2R,3S)-2-(3-Chloro-4-cyano-2-propylphenylamino)-3-hydroxybutanoic acid (intermediate 1119-A) (0.650 g, 2.19 mmol) and 4-cyanobenzohydrazide (0.353 g, 2.19 mmol) were mixed together in THF (100 ml) and cooled to –30° C. under N$_2$ atmosphere. To the pre-cooled reaction mixture were added hydroxybenzotriazole (HOBT) (0.335 g, 2.19 mmol), TEA (0.61 mL, 4.38 mmol) followed by N-(3-Dimethylaminopropyl)-N'-ethylcarbodiimide hydrochloride (EDCI) (0.840 g, 4.38 mmol). The reaction mixture was allowed to stir at –30° C. for 1 h and then at room temperature for 5 days. The reaction mixture was then quenched with 5% aq. citric acid and partitioned between water and EtOAc. The layers were separated and the organic extract was washed with 5% aq. citric acid twice, sat. aq. NaHCO$_3$, water, and concentrated in vacuo to yield the crude hydrazide product (0.710 g, 73%), which was carried on to the next synthetic step without further purification.

Intermediate 4c

N'-((2R,3S)-3-(tert-Butyldimethylsilyloxy)-2-(3-chloro-4-cyano-2-propylphenylamino)butanoyl)-4-cyanobenzohydrazide

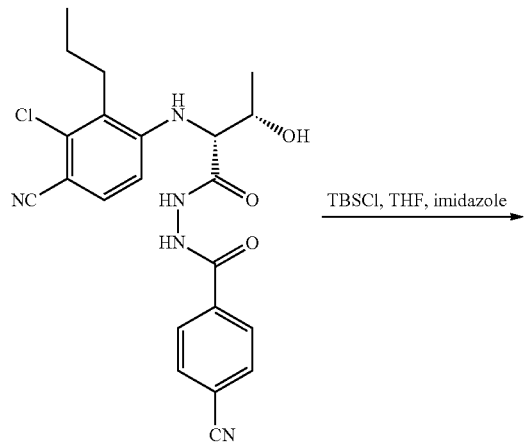

A 250 mL round bottom flask was charged with N'-((2R,3S)-2-(3-chloro-4-cyano-2-propylphenylamino)-3-hydroxybutanoyl)-4-cyanobenzohydrazide (intermediate 1119-B) (0.710 g, 1.61 mmol) and THF (20 mL) at room temperature. Imidazole (0.440 g, 6.47 mmol) and tert-butyldimethyl silyl chloride (0.730 g, 4.84 mmol) were then added to the mixture which was stirred at room temperature for 48 h. Water (20 mL) was then added to the mixture followed by heptane (50 mL) and stirred for 30 min at room temperature. EtOAc (50 mL) was then added and the phases were partitioned. The organic extract was separated, dried over $Na_2SO_4$, and concentrated to furnish a yellow solid. The crude material was purified by flash column chromatography [$SiO_2$, EtOAc-hexanes (20%:80%)→EtOAc-hexanes (50%:50%)→EtOAc-hexanes (60%:40%) as eluent] to afford the title compound as

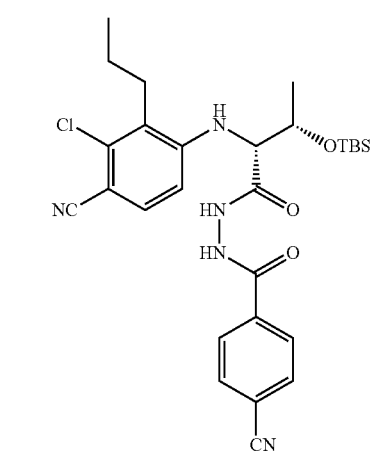

a light yellow solid with other minor impurities (0.750 g, 84% yield), which was immediately taken to the next synthetic step.

Intermediate 4d 4-((1R,2S)-2-(tert-Butyldimethylsilyloxy)-1-(5-(4-cyanophenyl)-1,3,4-oxadiazol-2-yl)propylamino-2-chloro-3-propylbenzonitrile

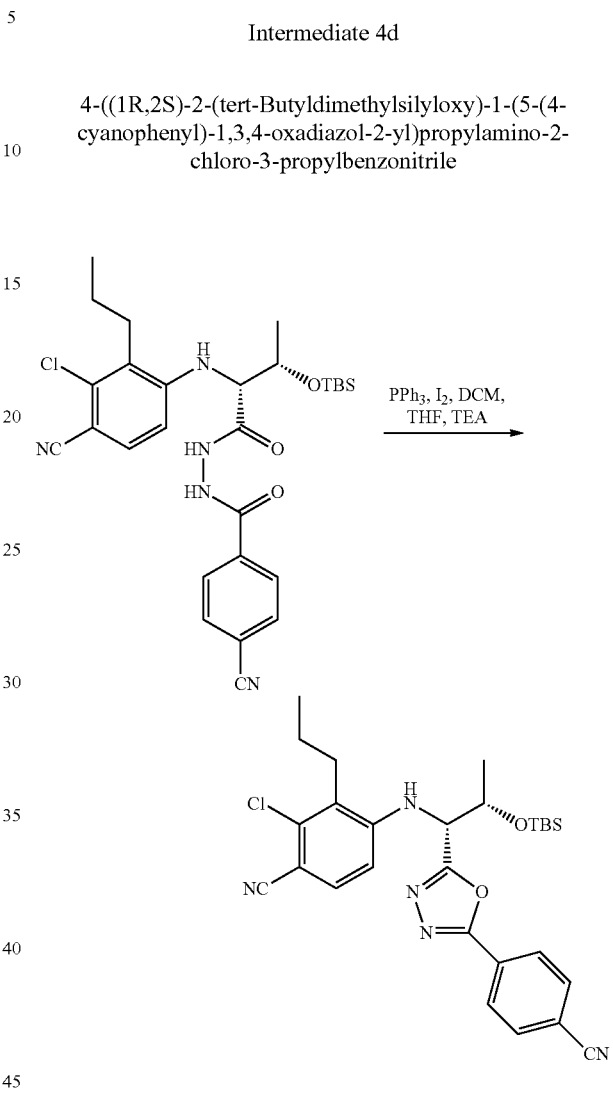

Triphenylphosphine (0.710 g, 2.71 mmol) was dissolved in 10 mL of DCM followed by addition of $I_2$ (0.687 g, 2.71 mmol) and TEA (0.75 mL, 5.41 mmol) at −15° C. N'-((2R,3S)-3-(tert-Butyldimethylsilyloxy)-2-(3-chloro-4-cyano-2-propylphenylamino)butanoyl)-4-cyanobenzohydrazide (intermediate 1119-C) (0.750 g, 1.35 mmol) in 20 ml DCM and 10 mL THF was added to the pre-cooled solution mixture of the $PPh_3/I_2$/TEA system and stirred. The temperature was allowed to warm to room temperature and stirred overnight. The reaction was quenched with citric acid (0.260 g) and $Na_2SO_3$ (0.170 g) in 50 mL of water and the biphasic mixture was separated. The aqueous layer was extracted with EtOAc (3×20 mL) and the combined organic extracts were washed with sat. aq. $NaHCO_3$, brine, dried over $Na_2SO_4$, filtered, and concentrated in vacuo. The resulting brown solid was purified by flash chromatography ($SiO_2$, [EtOAc-hexanes (20%:80%) →EtOAc-hexanes (50%:50%) as eluent]) to provide the title compound with other minor impurities (0.344 g, 47%). $^1H$ NMR (400 MHz, Acetone $d_6$, δ in ppm): 8.20 (d, J=8.0 Hz, 2H), 8.01 (d, J=8.0 Hz, 2H), 7.45 (d, J=8.0 Hz, 1H), 6.82 (d, J=8.0 Hz, 1H), 5.58 (d, J=8.0 Hz, 1H), 5.32 (dd, J=2.0, 8.0 Hz, 1H), 4.78 (m, 1H), 2.87 (t, J=8.0 Hz, 2H), 1.73 (m, 2H), 1.50 (d, J=4.0 Hz, 3H), 1.11 (t, J=8.0 Hz, 3H), 0.84 (s, 9H), 0.10 (s, 3H), −0.20 (s, 3H).

Example 4

2-Chloro-4-((1R,2S)-1-(5-(4-cyanophenyl)-1,3,4-oxadiazol-2-yl)-2-hydroxypropylamino)-3-propyl-benzonitrile

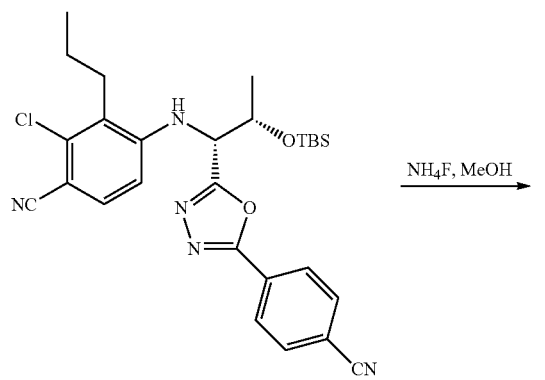

A 100 mL round bottom was charged with 4-((1R,2S)-2-(tert-butyldimethylsilyloxy)-1-(5-(4-cyanophenyl)-1,3,4-oxadiazol-2-yl)propylamino-2-chloro-3-propylbenzonitrile (intermediate 1119-D) (0.344 g, 0.64 mmole) and methanol (10 mL) at room temperature. Ammonium fluoride (0.119 g, 3.20 mmol) was then added in one portion and the reaction mixture was brought to reflux. The reaction stirred at reflux for 65 h before being cooled to room temperature. To the resulting reaction mixture was added water (50 mL), TBME (30 mL), EtOAc (50 mL) and more water (40 mL). The biphasic mixture was separated and the aqueous layer was extracted with EtOAc (50 mL). The organic extracts were then combined, washed with water (50 mL), dried over Na$_2$SO$_4$, filtered, and concentrated under reduced pressure to provide a brown solid. The brown solid was then purified by flash chromatography over silica gel [EtOAc-hexanes (50%:50%)→EtOAc-hexanes (100%:0%) as eluent] to provide the title compound with other minor impurities (200.7 mg, 74%). $^1$H NMR (400 MHz, CDCl$_3$ δ in ppm): 8.07 (d, J=8.0 Hz, 2H), 7.77 (d, J=8.0 Hz, 2H), 7.34 (d, J=8.0 Hz, 1H), 6.60 (d, J=8.0 Hz, 1H), 5.45 (d, J=8.0 Hz, 1H), 4.80 (d, J=2.0, 8.0 Hz, 1H), 4.60 (m, 1H), 2.79 (t, J=8.0 Hz, 2H), 1.64 (sextet, J=8.0 Hz, 2H), 1.46 (d, J=4.0 Hz, 3H), 1.07 (t, J=8.0 Hz, 3H).

Example 5

(R)-2-chloro-4-(1-(5-(4-fluorophenyl)-1,3,4-oxadiazol-2-yl)-2-hydroxy-2-methylpropylamino)-3-methylbenzonitrile

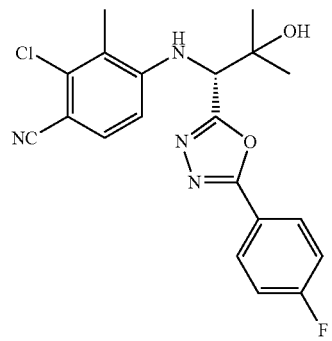 [SMILES: Cc1c(N[C@@H](c2nnc(-c3ccc(F)cc3)o2)C(C)(C)O)ccc(C#N)c1Cl]

Intermediate 5a (R)—N'-(2-(3-chloro-4-cyano-2-methylphenylamino)-3-hydroxy-3-methylbutanoyl)-4-fluorobenzohydrazide

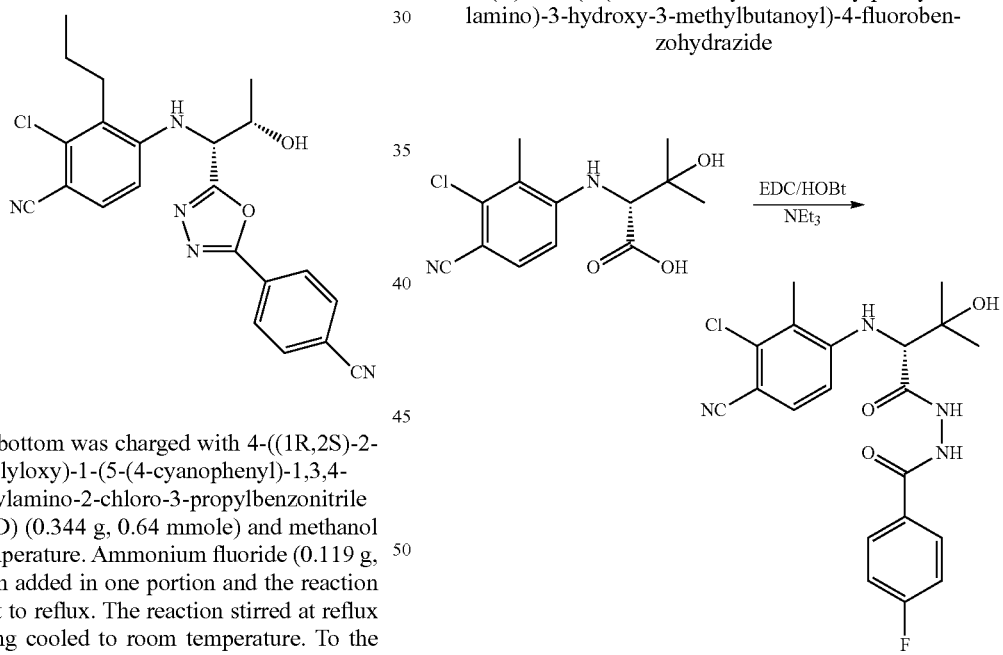

To a solution of (R)-2-(3-chloro-4-cyano-2-methylphenylamino)-3-hydroxy-3-methylbutanoic acid (4.0 g, 14.2 mmol) in THF (100 mL) were added 4-fluorobenzoic hydrazide (2.40 g, 15.6 mmol), HOBt (1.91 g, 14.1 mmol), EDC (4.07 g, 21.2 mmol) and Et$_3$N (3.0 mL, 21.5 mmol) at −20° C. sequentially. After addition, the mixture was stirred at −20° C. for 30 min., then room temperature overnight. The reaction was quenched by adding ice-water. After removal of the THF, the residue was extracted with EtOAc (300 mL). The EtOAc extracts were washed with water, brine and dried over Na$_2$SO$_4$. The filtrate was concentrated and purified by flash chromatography to give the title compound (R)—N'-(2-(3- chloro-4-cyano-2-methylphenylamino)-3-hydroxy-3-methylbutanoyl)-4-fluorobenzohydrazide (4.28 g, 72%). ¹H NMR (400 MHz, Acetone-d₆, δ in ppm) 9.61 (b, 2H), 8.00 (dd, J=5.5, 9.0 Hz, 2H), 7.51 (d, J=8.6 Hz, 1H), 7.25 (t, J=9.0 Hz, 2H), 6.71 (d, J=8.6 Hz, 1H), 5.53 (d, J=7.4 Hz, 1H), 4.06 (d, J=7.4 Hz, 1H), 2.35 (s, 3H), 1.45 (s, 3H), 1.40 (s, 3H).

Example 5

(R)-2-chloro-4-(1-(5-(4-fluorophenyl)-1,3,4-oxadiazol-2-yl)-2-hydroxy-2-methylpropylamino)-3-methylbenzonitrile

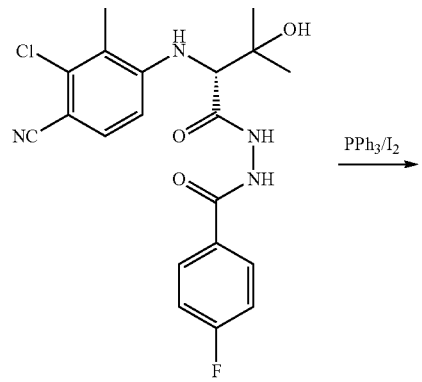

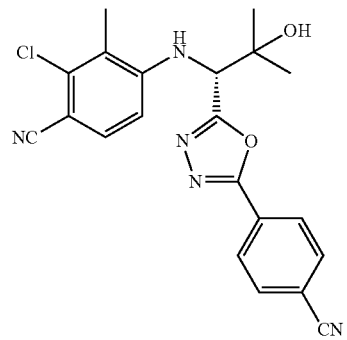 [SMILES: Cc1c(N[C@@H](c2nnc(-c3ccc(C#N)cc3)o2)C(C)(C)O)ccc(C#N)c1Cl]

To a solution of triphenylphosphine (5.35 g, 20.4 mmol) in DCM (100 mL) was added I₂ (5.18 g, 20.4 mmol) at 0° C. After all the Iodine was dissolved completely, Et₃N (5.7 mL, 40.9 mmol) was added, followed by a solution of (R)—N'-(2-(3-chloro-4-cyano-2-methylphenylamino)-3-hydroxy-3-methylbutanoyl)-4-fluorobenzohydrazide (4.27 g, 10.2 mmol) in DCM (20 mL) and THF (20 mL). After addition, the reaction mixture was allowed to warm to room temperature and stirred for additional 30 min. The reaction was quenched with saturated aq. sodium thiosulfate (20 mL) and diluted with DCM (100 mL). The organic layer was separated and washed with water, brine and dried over Na₂SO₄. After the solvent was removed, the residue was purified by flash chromatography to provide the title compound (R)-2-chloro-4-(1-(5-(4-fluorophenyl)-1,3,4-oxadiazol-2-yl)-2-hydroxy-2-methylpropylamino)-3-methylbenzonitrile (3.31 g, 81%). ¹H NMR (400 MHz, Acetone-d₆, δ in ppm) 8.06 (dd, J=5.3, 9.0 Hz, 2H), 7.47 (d, J=8.6 Hz, 1H), 7.33 (t, J=9.0 Hz, 2H), 6.79 (d, J=8.6 Hz, 1H), 5.70 (d, J=8.7 Hz, 1H), 5.09 (d, J=8.7 Hz, 1H), 2.39 (s, 3H), 1.52 (s, 3H), 1.36 (s, 3H).

Example 6

(R)-2-chloro-4-(1-(5-(4-cyanophenyl)-1,3,4-oxadiazol-2-yl)-2-hydroxy-2-methylpropylamino)-3-methylbenzonitrile Intermediate 6a (R)—N'-(2-(3-chloro-4-cyano-2-methylphenylamino)-3-hydroxy-3-methylbutanoyl)-4-cyanobenzohydrazide

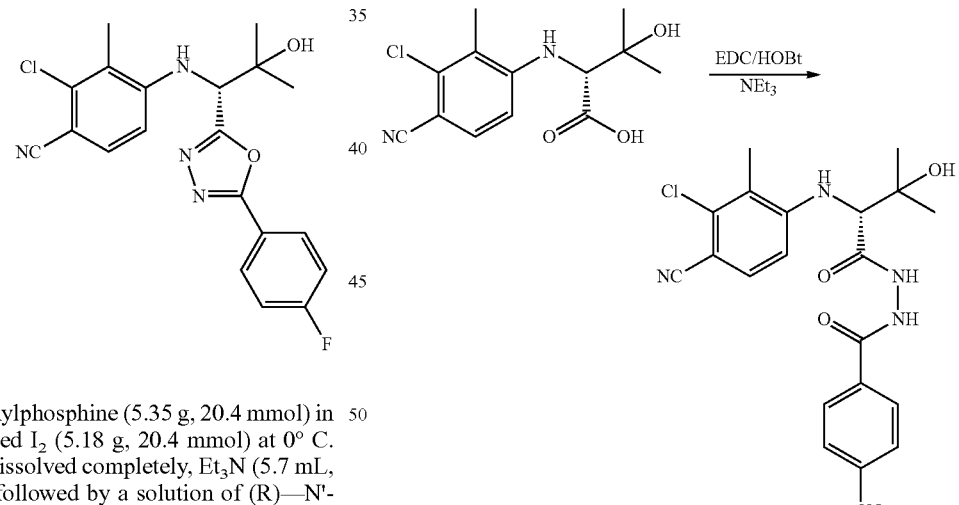

To a solution of (R)-2-(3-chloro-4-cyano-2-methylphenylamino)-3-hydroxy-3-methylbutanoic acid (3.5 g, 12.4 mmol) in THF (80 mL) were added 4-cyanobenzhydrazide (2.3 g, 14.3 mmol), HOBt (1.70 g, 12.6 mmol), EDC (3.56 g, 18.6 mmol) and Et₃N (2.8 mL, 20.1 mmol) at −20° C. sequentially. After addition, the mixture was stirred at −20° C. for 30 min., then room temperature overnight. The reaction was quenched by adding ice-water. After removal of the THF, the residue was extracted with EtOAc (300 mL). The EtOAc extracts were washed with water, brine and dried over Na₂SO₄. The filtrate was concentrated and purified by flash chromatography to give the title compound (R)—N'-(2-(3- chloro-4-cyano-2-methylphenylamino)-3-hydroxy-3-methylbutanoyl)-4-cyanobenzohydrazide (3.47 g, 65%). $^1$H NMR (400 MHz, Acetone-$d_6$, δ in ppm) 9.72 (b, 2H), 8.08 (d, J=8.4 Hz, 2H), 7.92 (d, J=8.4 Hz, 2H), 7.52 (d, J=8.6 Hz, 1H), 6.72 (d, J=8.6 Hz, 1H), 5.55 (d, J=7.2 Hz, 1H), 4.08 (d, J=7.2 Hz, 1H), 2.35 (s, 3H), 1.47 (s, 3H), 1.42 (s, 3H).

Example 6

(R)-2-chloro-4-(1-(5-(4-cyanophenyl)-1,3,4-oxadiazol-2-yl)-2-hydroxy-2-methylpropylamino)-3-methylbenzonitrile

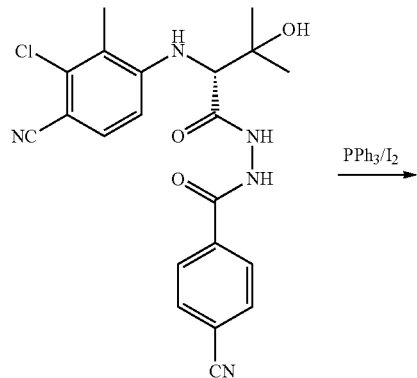

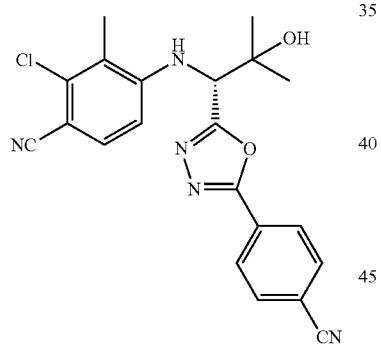

To a solution of triphenylphosphine (1.70 g, 6.48 mmol) in DCM (50 mL) was added I$_2$ (1.63 g, 6.42 mmol) at 0° C. After all the Iodine was dissolved completely, Et$_3$N (1.8 mL, 12.9 mmol) was added, followed by a solution of (R)—N'-(2-(3-chloro-4-cyano-2-methylphenylamino)-3-hydroxy-3-methylbutanoyl)-4-cyanobenzohydrazide (1.37 g, 3.22 mmol) in DCM (10 mL) and THF (10 mL). After addition, the reaction mixture was allowed to warm to room temperature and stirred for additional 30 min. The reaction was quenched with saturated aq. sodium thiosulfate (10 mL) and diluted with DCM (100 mL). The organic layer was separated and washed with water, brine and dried over Na$_2$SO$_4$. After the solvent was removed, the residue was purified by flash chromatography to provide the title compound (R)-2-chloro-4-(1-(5-(4-cyanophenyl)-1,3,4-oxadiazol-2-yl)-2-hydroxy-2-methylpropylamino)-3-methylbenzonitrile (1.18 g, 90%). $^1$H NMR (400 MHz, Acetone-$d_6$, δ in ppm) 8.19 (d, J=8.8 Hz, 2H), 7.97 (d, J=8.8 Hz, 2H), 7.46 (d, J=8.6 Hz, 1H), 6.80 (d, J=8.6 Hz, 1H), 5.71 (d, J=9.0 Hz, 1H), 5.14 (d, J=9.0 Hz, 1H), 4.67 (s, 1H), 2.39 (s, 3H), 1.53 (s, 3H), 1.36 (s, 3H).

Example 7

2-chloro-4-((1R,2S)-1-(5-(4-cyanophenyl)-1,3,4-oxadiazol-2-yl)-3,3,3-trifluoro-2-hydroxypropylamino)-3-methylbenzonitrile

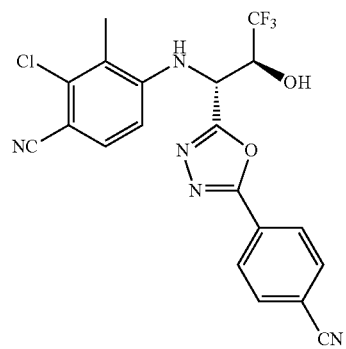 [SMILES: Cc1c(N[C@@H](c2nnc(-c3ccc(C#N)cc3)o2)[C@H](O)C(F)(F)F)ccc(C#N)c1Cl]

Intermediate 7a (S)-tert-butyl 2,2-dimethyl-4-(2,2,2-trifluoro-1-hydroxyethyl)oxazolidine-3-carboxylate

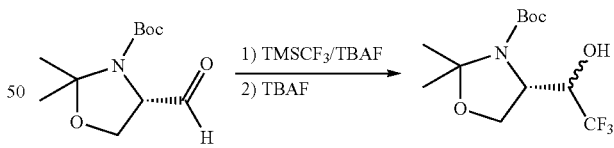

To a mixture of (S)-4-formyl-2,2-dimethyl-oxazolidine-3-carboxylic acid tert-butyl ester (1.0 g, 4.36 mmol), (trifluoromethyl)trimethylsilane (2.0 M solution in THF, 2.6 mL, 5.20 mmol) in THF (10 mL) was added tetrabutylammonium fluoride (1.0 M solution in THF, 0.1 mL, 0.10 mmol) at 0° C. After addition, the mixture was stirred at room temperature for 60 h. Then, tetrabutylammonium fluoride (1.0 M solution in THF, 9 mL, 9.0 mmol) was added and the mixture stirred for another 6 h and subsequently quenched by adding saturated aq. NaHCO$_3$ solution, extracted with EtOAc. The extracts were washed with saturated aq. NaHCO$_3$ solution, water, brine and dried over Na$_2$SO$_4$. Concentration and purification gave (S)-tert-butyl 2,2-dimethyl-4-(2,2,2-trifluoro- 1-hydroxyethyl)oxazolidine-3-carboxylate (1.21 g, 92%), which showed a complicated NMR spectrum because of the different comformers.

Intermediate 7b (S)-tert-butyl 4-((R)-1-(benzyloxy)-2,2,2-trifluoroethyl)-2,2-dimethyloxazolidine-3-carboxylate

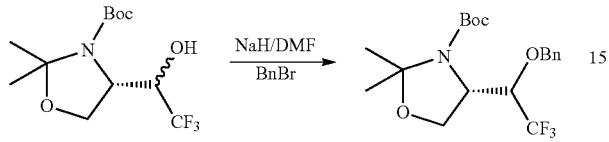

To a suspension of NaH (60% in mineral oil, 300.0 mg, 7.50 mmol) in DMF (20 mL) was added (S)-tert-butyl 2,2-dimethyl-4-(2,2,2-trifluoro-1-hydroxyethyl)oxazolidine-3-carboxylate (1.09 g, 3.64 mmol) in DMF (20 mL) and the mixture was stirred at room temperature for 1 h. Then, benzyl bromide (0.86 mL, 7.23 mmol) was added and the mixture was stirred at room temperature overnight then quenched with ice-water, extracted with EtOAc. The organic extracts were washed with water, brine and dried over Na$_2$SO$_4$. Removal of the solvent gave a residue, which was purified by silica gel chromatography to give (S)-tert-butyl 4-((R)-1-(benzyloxy)-2,2,2-trifluoroethyl)-2,2-dimethyloxazolidine-3-carboxylate (1.21 g, 85%), which showed a complicated NMR spectrum because of the different rotamers. $^1$H NMR (400 MHz, CDCl$_3$, δ in ppm) 7.28~7.33 (m, 5H), 4.60~4.85 (m, 3H), 3.93~4.23 (m, 3H), 1.42~1.65 (m, 15H).

Intermediate 7c

Tert-butyl (2S,3S)-3-(benzyloxy)-4,4,4-trifluoro-1-hydroxybutan-2-ylcarbamate

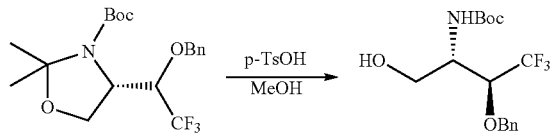 [SMILES: "MeOH" ; CC(C)(C)OC(=O)N1[C@H](C(OCc2ccccc2)C(F)(F)F)COC1(C)C ; CC(C)(C)OC(=O)N[C@@H](CO)[C@H](OCc1ccccc1)C(F)(F)F]

To a solution of (S)-tert-butyl 4-((R)-1-(benzyloxy)-2,2,2-trifluoroethyl)-2,2-dimethyloxazolidine-3-carboxylate (1.21 g, 3.1 mmol) in methanol (100 mL) was added p-toluenesulfonic acid monohydrate (90 mg, 0.47 mmol). The mixture was stirred at room temperature for 5 days, then the methanol was removed and the residue was dissolved with EtOAc. The EtOAc solution was washed with saturated aq. Na$_2$CO$_3$ solution, water, brine and dried over Na$_2$SO$_4$. Removal of the solvent gave a residue which was purified by flash chromatography to afford the title compound tert-butyl (2S,3S)-3-(benzyloxy)-4,4,4-trifluoro-1-hydroxybutan-2-ylcarbamate (0.54 g, 90%) and recovered starting material (0.54 g). $^1$H NMR (400 MHz, CDCl$_3$, □ in ppm) 7.31~7.39 (m, 5H), 5.21 (d, J=7.6 Hz, 1H), 4.87 (d, J=11.1 Hz, 1H), 4.58 (d, J=11.1 Hz, 1H), 4.13 (m, 1H), 4.00 (d, J=11.7 Hz, 1H), 3.83 (m, 1H), 3.65 (d, J=11.7 Hz, 1H), 1.40 (s, 9H).

Intermediate 7d (2R,3S)-3-(benzyloxy)-2-(tert-butoxycarbonylamino)-4,4,4-trifluorobutanoic acid

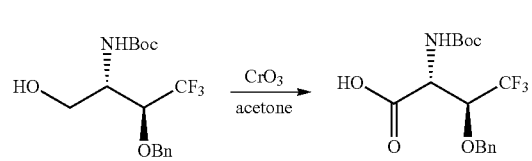

To a solution of tert-butyl (2S,3S)-3-(benzyloxy)-4,4,4-trifluoro-1-hydroxybutan-2-ylcarbamate (1.47 g, 4.2 mmol) in acetone (80 mL) was added Jone's reagent (8.2 mL) at 0° C. The mixture was stirred at the same temperature for 3 h until the starting material was completely consumed, then the reaction was quenched by adding isopropanol (5 mL). The reaction mixture was extracted with EtOAc. The extracts were washed with water, brine and dried over Na$_2$SO$_4$. Removal of the solvent gave the crude (2R,3S)-3-(benzyloxy)-2-(tert-butoxycarbonylamino)-4,4,4-trifluorobutanoic acid (1.56 g), which was used directly for the following reaction. $^1$H NMR (400 MHz, CD$_3$OD, δ in ppm) 7.25~7.34 (m, 5H), 4.76 (d, J=10.9 Hz, 1H), 4.70 (d, J=10.9 Hz, 1H), 4.53 (d, J=6.4 Hz, 1H), 4.32 (m, 1H), 1.41 (s, 9H).

Intermediate 7e (2R,3S)-2-amino-3-(benzyloxy)-4,4,4-trifluorobutanoic acid hydrochloride

To a solution of (2R,3S)-3-(benzyloxy)-2-(tert-butoxycarbonylamino)-4,4,4-trifluorobutanoic acid (1.56 g, 4.2 mmol) in EtOAc (30 mL) was added EtOAc saturated with hydrogen chloride (30 mL) at 0° C. Then, the mixture was stirred at room temperature for 1.5 h. After concentration of the reaction mixture to about 15 mL, the white solid was collected by filtration and washed with EtOAc, dried in vacuum to give the title compound (2R,3S)-2-amino-3-(benzyloxy)-4,4,4-trifluorobutanoic acid hydrochloride salt (1.06 g, 84% for two steps). ¹H NMR (400 MHz, CD₃OD, δ in ppm) 7.32~7.44 (m, 5H), 4.86 (d, J=2.0 Hz, 2H), 4.70 (dq, J=3.6, 6.6 Hz, 1H), 4.50 (d, J=3.6 Hz, 1H).

Intermediate 7f (2R,3S)-3-(benzyloxy)-2-(3-chloro-4-cyano-2-methylphenylamino)-4,4,4-trifluorobutanoic acid

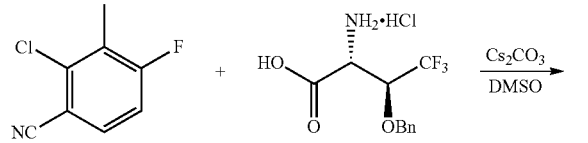

Cs₂CO₃ (3.5 g, 10.7 mmol) was added to a mixture of 2-chloro-4-fluoro-3-methylbenzonitrile (0.79 g, 4.65 mmol) and (2R,3S)-2-amino-3-(benzyloxy)-4,4,4-trifluorobutanoic acid hydrochloride salt (0.93 g, 3.1 mmol) in DMSO (18 mL) at room temperature. The resulting mixture was heated to 80° C. and stirred for 2 days. After cooling to room temperature, the reaction mixture was poured into ice-water (150 mL) and extracted with 10% EtOAc in hexanes (2×50 mL). The aqueous phase was acidified to pH=2~3 with 2N HCl and extracted with EtOAc (2×100 mL). The EtOAc extracts were washed with water, brine and dried over Na₂SO₄. Removal of the solvent gave a residue, which was purified by flash chromatography to afford the crude (2R,3S)-3-(benzyloxy)-2-(3-chloro-4-cyano-2-methylphenylamino)-4,4,4-trifluorobutanoic acid (280 mg) as a mixture.

Intermediate 7g

N'-((2R,3S)-3-(benzyloxy)-2-(3-chloro-4-cyano-2-methylphenylamino)-4,4,4-trifluorobutanoyl)-4-cyanobenzohydrazide

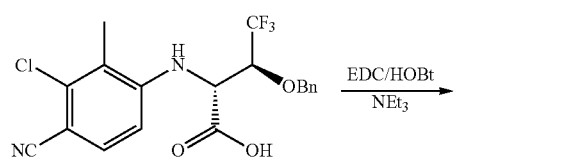

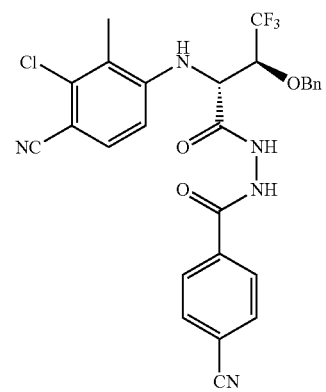

To a solution of (2R,3S)-3-(benzyloxy)-2-(3-chloro-4-cyano-2-methylphenylamino)-4,4,4-trifluorobutanoic acid (280 mg) in THF (15 mL) were added 4-cyanobenzohydrazide (130 mg, 0.81 mmol), HOBt (109 mg, 0.81 mmol), EDC (232 mg, 1.21 mmol) and Et₃N (0.25 mL, 1.79 mmol) at −20° C. sequentially. After addition, the mixture was stirred at −20° C. for 30 min., then room temperature overnight. The reaction was quenched by adding ice-water. After removal of the THF, the residue was extracted with EtOAc (200 mL). The EtOAc extracts were washed with water, brine and dried over Na₂SO₄. The filtrate was concentrated and purified by flash chromatography to give the title compound N'-((2R,3S)-3-(benzyloxy)-2-(3-chloro-4-cyano-2-methylphenylamino)-4,4,4-trifluorobutanoyl)-4-cyanobenzohydrazide (180 mg, 10%). ¹H NMR (400 MHz, CDCl₃, δ in ppm) 9.26 (b, 1H), 8.88 (b, 1H), 7.92 (d, J=8.4 Hz, 2H), 7.74 (d, J=8.4 Hz, 2H), 7.36~7.39 (m, 5H), 7.28 (d, J=8.7 Hz, 1H), 6.44 (d, J=8.7 Hz, 1H), 5.22 (d, J=6.6 Hz, 1H), 4.93 (d, J=11.1 Hz, 1H), 4.80 (d, J=11.1 Hz, 1H), 4.66 (m, 1H), 4.33 (d, J=6.6 Hz, 1H), 2.27 (s, 3H).

Intermediate 7h 4-((1R,2S)-2-(benzyloxy)-1-(5-(4-cyanophenyl)-1,3,4-oxadiazol-2-yl)-3,3,3-trifluoropropylamino)-2-chloro-3-methylbenzonitrile

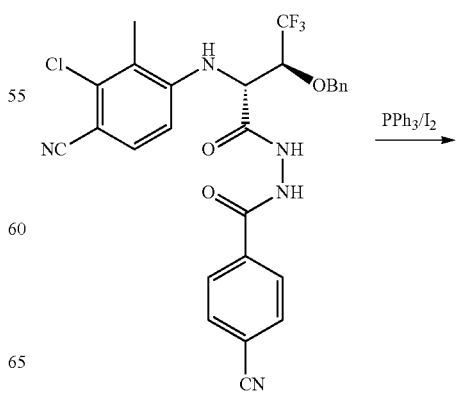

-continued

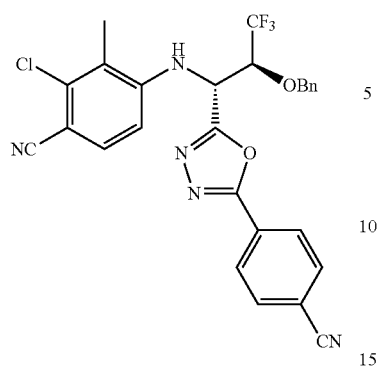

To a solution of triphenylphosphine (180 mg, 0.69 mmol) in DCM (10 mL) was added I$_2$ (174 mg, 0.69 mmol) at 0° C. After all the Iodine was dissolved completely, Et$_3$N (0.20 mL, 1.43 mmol) was added, followed by a solution of N'-((2R, 3S)-3-(benzyloxy)-2-(3-chloro-4-cyano-2-methylphenylamino)-4,4,4-trifluorobutanoyl)-4-cyanobenzohydrazide (180 mg, 0.32 mmol) in DCM (2 mL) and THF (2 mL). After addition, the reaction mixture was allowed to warm to room temperature and stirred for an additional 30 min. The reaction was quenched with saturated aq. sodium thiosulfate (1 mL) and diluted with DCM (100 mL). The organic layer was separated and washed with water, brine and dried over Na$_2$SO$_4$. After the solvent was removed, the residue was purified by flash chromatography to provide the title compound 4-((1R,2S)-2-(benzyloxy)-1-(5-(4-cyanophenyl)-1,3,4-oxadiazol-2-yl)-3,3,3-trifluoropropylamino)-2-chloro-3-methylbenzonitrile (170 mg, 98%). $^1$H NMR (400 MHz, CDCl$_3$, δ in ppm) 7.98 (d, J=8.8 Hz, 2H), 7.80 (d, J=8.8 Hz, 2H), 7.36 (d, J=8.4 Hz, 1H), 7.09~7.17 (m, 5H), 6.45 (d, J=8.4 Hz, 1H), 5.22 (b, 2H), 5.01 (d, J=11.5 Hz, 1H), 4.69 (d, J=11.5 Hz, 1H), 4.52 (m, 1H), 2.34 (s, 3H).

Example 7

2-chloro-4-((1R,2S)-1-(5-(4-cyanophenyl)-1,3,4-oxadiazol-2-yl)-3,3,3-trifluoro-2-hydroxypropylamino)-3-methylbenzonitrile

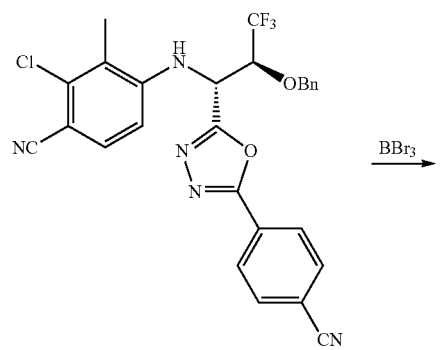

-continued

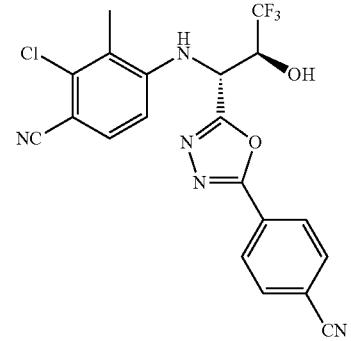

To a solution of 4-((1R,2S)-2-(benzyloxy)-1-(5-(4-cyanophenyl)-1,3,4-oxadiazol-2-yl)-3,3,3-trifluoropropylamino)-2-chloro-3-methylbenzonitrile (170 mg, 0.32 mmol) in DCM (15 mL) was added BBr$_3$ (380 mg, 1.52 mmol) in 0.7 mL DCM at 0° C. The reaction mixture was stirred at 0° C. for 2 h until the starting material completely disappeared. The reaction was quenched with saturated aq. NaHCO$_3$ solution, extracted with EtOAc. The EtOAc extracts were washed with water, brine and dried over Na$_2$SO$_4$. After the solvent was removed, the residue was purified by flash chromatography to provide the title compound 2-chloro-4-((1R,2S)-1-(5-(4-cyanophenyl)-1,3,4-oxadiazol-2-yl)-3,3,3-trifluoro-2-hydroxypropylamino)-3-methylbenzonitrile (74.6 mg, 53%) as a white solid. $^1$H NMR (400 MHz, Acetone-d$_6$, δ in ppm) 8.23 (d, J=8.6 Hz, 2H), 8.01 (d, J=8.6 Hz, 2H), 7.55 (d, J=8.6 Hz, 1H), 7.06 (d, J=8.6 Hz, 1H), 6.73 (b, 1H), 5.77 (d, J=9.4 Hz, 1H), 5.72 (dd, J=2.4, 9.0 Hz, 1H), 5.21 (m, 1H), 2.40 (s, 3H).

The binding data shown in table 1 (below) is from the result of a single or multiple determinations based on the same compound. Where multiple data points have been taken, the value reported is the average of the multiple determinations.

TABLE 1

Compound AR-Binding Affinity

| Compound | Binding IC$_{50}$ (nM) |
|---|---|
| Example 1 | >1000 |
| Example 2 | 40 |
| Example 3 | 30 |
| Example 4 | 0.3 |
| Example 5 | 6 |
| Example 6 | 4 |
| Example 7 | 290 |

In Vivo Activity—Rat Herschberger Assay

In vivo utility of the compounds of this invention may be demonstrated through use of various in vivo animal models including the Herschberger assay. Selected data from Example 7 is shown in the FIGURE. As shown in the FIGURE, at a dose of 3 mg/kg (orally), compound 5 increased levator ani muscle (LABC) in a castrated rat to a level significantly above the non-castrated control (Sham) and testosterone propionate-treated (TP) controls.

What is claimed is:
1. A compound selected from:
(R)-4-(1-(5-(4-fluorophenyl)-1,3,4-oxadiazol-2-yl)-2-hydroxy-2-methylpropylamino)-2-(trifluoromethyl)benzonitrile;
(R)-4-(1-(5-(4-fluorophenyl)-1,3,4-oxadiazol-2-yl)-2-hydroxy-2-methylpropylamino)-3-methyl-2-(trifluoromethyl)benzonitrile;

(R)-4-(1-(5-(4-cyanophenyl)-1,3,4-oxadiazol-2-yl)-2-hydroxy-2-methylpropylamino)-3-methyl-2-(trifluoromethyl)benzonitrile;

(R)-2-chloro-4-(1-(5-(4-fluorophenyl)-1,3,4-oxadiazol-2-yl)-2-hydroxy-2-methylpropylamino)-3-methylbenzonitrile; and (R)-2-chloro-4-(1-(5-(4-cyanophenyl)-1,3,4-oxadiazol-2-yl)-2-hydroxy-2-methylpropylamino)-3-methylbenzonitrile;

or pharmaceutically acceptable salt of any of the foregoing.

2. A compound according to claim 1, selected from:

(R)-2-chloro-4-(1-(5-(4-fluorophenyl)-1,3,4-oxadiazol-2-yl)-2-hydroxy-2-methylpropylamino)-3-methylbenzonitrile; and (R)-2-chloro-4-(1-(5-(4-cyanophenyl)-1,3,4-oxadiazol-2-yl)-2-hydroxy-2-methylpropylamino)-3-methylbenzonitrile, or a pharmaceutically acceptable salt of any of the foregoing.

3. A pharmaceutical composition comprising a compound according claim 1 and at least one pharmaceutically acceptable excipient.

4. A method of modulating an androgen receptor in a cell, comprising contacting a cell expressing the androgen receptor with a compound according to claim 1 or a pharmaceutically acceptable salt thereof.

5. A method of identifying a compound capable of modulating an androgen receptor comprising contacting a cell expressing an androgen receptor with a compound according to claim 1, and monitoring the effect of the compound on the cell.

6. A method of treating ameliorating the symptoms of sarcopenia, frailty, cachexia, muscular dystrophy, low body weight, and AIDS wasting in a mammal in need thereof, comprising the administration to said mammal of an effective amount of a compound, or a pharmaceutically acceptable salt thereof, according to claim 1.

7. The method of claim 6, wherein the mammal is a human.

8. A method of modulating an androgen receptor in a cell, comprising contacting a cell expressing the androgen receptor with the pharmaceutical composition of claim 3.

9. A method of treating ameliorating the symptoms of sarcopenia, frailty, cachexia, muscular dystrophy, low body weight, and AIDS wasting in a mammal in need thereof, comprising the administration to said mammal of an effective amount of the pharmaceutical composition of claim 3.

10. 2-Chloro-4-((1R,2S)-1-(5-(4-cyanophenyl)-1,3,4-oxadiazol-2-yl)-2-hydroxypropylamino)-3-propylbenzonitrile, or pharmaceutically acceptable salt thereof.

11. 2-chloro-4-((1R,2S)-1-(5-(4-cyanophenyl)-1,3,4-oxadiazol-2-yl)-3,3,3-trifluoro-2-hydroxypropylamino)-3-methylbenzonitrile, or pharmaceutically acceptable salt thereof.

12. A pharmaceutical composition comprising a compound according claim 10 and at least one pharmaceutically acceptable excipient.

13. A pharmaceutical composition comprising a compound according claim 11 and at least one pharmaceutically acceptable excipient.

14. A method of modulating an androgen receptor in a cell, comprising contacting a cell expressing the androgen receptor with the compound according to claim 10 or a pharmaceutically acceptable salt thereof.

15. A method of modulating an androgen receptor in a cell, comprising contacting a cell expressing the androgen receptor with the compound according to claim 11 or a pharmaceutically acceptable salt thereof.

16. A method of ameliorating the symptoms of sarcopenia, frailty, cachexia, muscular dystrophy, low body weight, AIDS wasting in a mammal in need thereof, comprising the administration to said mammal of an effective amount of a compound, or a pharmaceutically acceptable salt thereof, according to claim 10.

17. A method of ameliorating the symptoms of sarcopenia, frailty, cachexia, muscular dystrophy, low body weight, and AIDS wasting in a mammal in need thereof, comprising the administration to said mammal of an effective amount of a compound, or a pharmaceutically acceptable salt thereof, according to claim 11.

18. The method of claim 16 wherein the mammal is a human.

19. The method of claim 17, wherein the mammal is a human.

20. A method of modulating an androgen receptor in a cell, comprising contacting a cell expressing the androgen receptor with the pharmaceutical composition of claim 12.

21. A method of modulating an androgen receptor in a cell, comprising contacting a cell expressing the androgen receptor with the pharmaceutical composition of claim 13.

22. A method of ameliorating the symptoms of sarcopenia, frailty, cachexia, muscular dystrophy, low body weight, and AIDS wasting in a mammal in need thereof, comprising the administration to said mammal of an effective amount of the pharmaceutical composition of claim 12.

23. A method of ameliorating the symptoms of sarcopenia, frailty, cachexia, muscular dystrophy, low body weight, and AIDS wasting in a mammal in need thereof, comprising the administration to said mammal of an effective amount of the pharmaceutical composition of claim 13.

24. A method of identifying a compound capable of modulating an androgen receptor comprising contacting a cell expressing an androgen receptor with a compound according to claim 10, and monitoring the effect of the compound on the cell.

25. A method of identifying a compound capable of modulating an androgen receptor comprising contacting a cell expressing an androgen receptor with a compound according to claim 11, and monitoring the effect of the compound on the cell.

26. The method of any one of claims 6, 9, 16, 17, 22 or 23, wherein the cachexia is cancer cachexia.

* * * * *